(12) United States Patent
Peterson et al.

(10) Patent No.: US 6,267,733 B1
(45) Date of Patent: Jul. 31, 2001

(54) APPARATUS AND METHODS FOR TREATING MOTOR CONTROL AND SOMATOSENSORY PERCEPTION DEFICITS

(75) Inventors: Bret E. Peterson, Lafayette; Barbara M. Calhoun, El Cerrito; Michael Mathias Merzenich, San Francisco; William M. Jenkins, Pacifica; Nancy Byl, Oakland; Srikantan Nagarajan, San Francisco, all of CA (US)

(73) Assignees: Scientific Learning Corporation, Berkeley; The Regents of the University of California, Oakland, both of CA (US)

( * ) Notice: Subject to any disclaimer, the term of this patent is extended or adjusted under 35 U.S.C. 154(b) by 0 days.

(21) Appl. No.: 09/374,227

(22) Filed: Aug. 13, 1999

Related U.S. Application Data

(63) Continuation-in-part of application No. 08/970,339, filed on Nov. 14, 1997, now abandoned.

(51) Int. Cl.$^7$ .................................................. A61B 5/103
(52) U.S. Cl. ............................ 600/587; 600/552; 600/595
(58) Field of Search .................................... 600/552, 553, 600/555, 557, 587, 594, 595; 434/112, 113, 114; 128/898

(56) References Cited

U.S. PATENT DOCUMENTS

| | | | |
|---|---|---|---|
| 4,392,496 | 7/1983 | Stanton | 607/48 |
| 4,467,815 | 8/1984 | O'Brien et al. | 600/553 |
| 4,690,142 | 9/1987 | Ross et al. | 128/905 |

(List continued on next page.)

FOREIGN PATENT DOCUMENTS

| | | | |
|---|---|---|---|
| WO 91/07133 | 5/1991 | (WO) | A51B/5/103 |
| WO 93/02622 | 2/1993 | (WO) | A61B/5/16 |
| WO 94/04072 | 3/1994 | (WO) | A61B/5/00 |

(List continued on next page.)

OTHER PUBLICATIONS

Andrew J. Saykin, PsyD, et al., "Neuropsychological Function in Schizophrenia–Selective Impairment in Memory and Learning", Arch Gen Psychiatry, vol. 48, Jul. 1991, pp. 618–624.

(List continued on next page.)

OTHER PUBLICATIONS

*Primary Examiner*—Cary O'Connor
*Assistant Examiner*—Charles Marmor, II
(74) *Attorney, Agent, or Firm*—Beyer Weaver & Thomas, LLP

(57) ABSTRACT

The present invention describes computer-implemented methods and apparatus for treating motor control and somatosensory perception deficits. The motor control and somatosensory perception deficits may have their genesis in a wide variety of issues ranging from injury, disease, or a gradual degradation of motor control over time due to repetitive strain, for example. By administering a computer-implemented training regime directed to improve sensory feedback and motor control, abnormal motor control and somatosensory perception may be substantially improved. The computer-implemented training regime includes somatosensory perception and motor control exercises which may be flexibly administered. Several training apparatus are described for implementing the somatosensory perception and motor control exercises. The training apparatus described herein are capable of driving improvements in temporal, spatial and intensity resolution of somatosensory feedback. In addition, the apparatus allow the training to be monitored and adapted on a quantitative basis as treatment proceeds. Advantageously, this provides a more accurate and effective training tool for treating motor control deficits. Further, the computer-implemented methods and apparatus allow treatment to be administered in the convenience of the person's own home and on a daily basis.

37 Claims, 8 Drawing Sheets

U.S. PATENT DOCUMENTS

| | | | |
|---|---|---|---|
| 4,763,666 | 8/1988 | Strian et al. | 600/555 |
| 4,811,742 | 3/1989 | Hassel et al. | 600/554 |
| 5,002,065 | 3/1991 | LaCourse et al. | 600/552 |
| 5,020,542 | 6/1991 | Rossmann et al. | 600/554 |
| 5,022,407 | 6/1991 | Horch et al. | 600/552 |
| 5,027,828 | 7/1991 | Kovacevic et al. | 600/552 |
| 5,078,152 | 1/1992 | Bond et al. | 128/774 |
| 5,191,896 | 3/1993 | Gafni et al. | 600/555 |
| 5,195,532 | 3/1993 | Schumacher et al. | 128/739 |
| 5,230,345 | 7/1993 | Curran et al. | 600/552 |
| 5,333,618 | 8/1994 | Lekhtman et al. | 600/554 |
| 5,337,757 | 8/1994 | Jain et al. | 128/779 |
| 5,363,859 | 11/1994 | Tuckett et al. | 600/552 |
| 5,381,805 | 1/1995 | Tuckett et al. | 600/552 |
| 5,410,472 | 4/1995 | Anderson | 364/413.04 |
| 5,522,386 | 6/1996 | Lerner | 600/557 |
| 5,533,514 | 7/1996 | Lavigne et al. | 600/557 |
| 5,673,703 | 10/1997 | Fisher et al. | 600/552 |
| 5,678,571 | 10/1997 | Brown | 128/898 |
| 5,692,906 | 12/1997 | Corder | 434/156 |
| 5,719,561 | 2/1998 | Gonzales | 340/825.46 |
| 5,720,711 | 2/1998 | Bond et al. | 601/23 |
| 5,722,418 | 3/1998 | Bro | 128/732 |
| 5,725,472 | 3/1998 | Weathers | 600/21 |
| 5,792,212 | 8/1998 | Weijand | 600/554 |
| 5,797,854 | 8/1998 | Hedgecock | 600/554 |
| 5,806,522 | 9/1998 | Katims | 600/554 |
| 5,830,158 | 11/1998 | Zanakis | 600/595 |
| 5,910,107 | 6/1999 | Iliff | 600/300 |
| 5,913,310 | 6/1999 | Brown | 128/897 |
| 5,919,149 | 7/1999 | Allum | 600/595 |
| 5,980,429 | 11/1999 | Nashner | 482/8 |
| 6,063,046 | 5/2000 | Allum | 600/595 |

FOREIGN PATENT DOCUMENTS

| | | | |
|---|---|---|---|
| WO 94/06088 | 3/1994 | (WO) | G06F/15/42 |
| WO 95/29447 | 11/1995 | (WO) | G06F/15/02 |
| WO 97/06730 | 2/1997 | (WO) | A61B/5/0484 |
| WO 97/34526 | 9/1997 | (WO) | A61B/5/05 |

OTHER PUBLICATIONS

Bruce E. Wexler, M.D., et al., "The Outpatient Treatment of Depression Implications of Outcome Research for Clinical Practice", The Journal of Nervous and Mental Disease, vol. 180, No. 5, May 1992, pp. 277–286.

Ralph H.B. Benedict, et al., "Effects of Attention Training on Information Processing in Schizophrenia", Schizophrenia Bulletin, vol. 20, No. 3, 1994, pp. 537–546.

Patrick W. Corrigan, et al., "Memory and vigilance training to improve social perception in schizophrenia", Schizophrenia Research, © 1995 Elsevier Science B.V., pp. 257–265.

Ian Creese, et al., "Dopamine Receptor Binding Predicts Clinical and Pharmacological Potencies of Antischizophrenic Drugs", © 1976 American Assoc. for the Advancement of Science, Apr. 30, 1976, vol. 192, pp. 481–483.

Ian Creese, et al., "Dopamine Receptors: A Classification", Dept. of Neurosciences, Journal of Clinical Psychopharmacology, © 1982 Williams & Wilkins Co., vol. 2, No. 5, pp. 329–335.

Ricardo Davila, PhD, et al., "Plasma Homovanillic Acid as a Predictor of Response to Neuroleptics", Arch Gen. Psychiatry, vol. 45, Jun. 1988, pp. 564–567.

Ann Delahunty, PhD., et al., "Rehabilitation of frontal/executive impairments in schizophrenia", Australian and New Zealand Journal Of Psychiatry, vol. 30, No. 6, Dec. 1996, pp. 760–767.

Colin D. Field et al., "Computer–Aided Cognitive Rehabilitation: Possible Application To The Attentional Deficit Of Schizophrenia, A Report Of Negative Results", © Perceptual and Motor Skills 1997, vol. 85, pp. 995–1002.

Michael F. Green Ph.D., "What Are the Functional Consequences of Neurocognitive Deficits in Schizophrenia?", Am J Psychiatry 153:3, Mar. 1996, pp. 321–330.

M. Hermanutz et al, "Computer–assisted Attention Training in Schizophrenics—A Comparative Study", © Springer–Verlag 1991, European Archives of Psychiatry and clinical Neuroscience 1991, pp. 282–287.

Amy R. Koreen, M.D., et al., "Plasma Homovanillic Acid Levels in First–Episode Schizophrenia—Psychopathology and Treatment Response", Arch Gen Psychiatry, vol. 51, Feb. 1994, pp. 132–138.

Heidi Nisbet et al., "Improving schizophrenic in–patients' Wisconsin card–sorting performance", © 1996 The British Psychological Society, British Journal Of Clinical Psychology (1996) vol. 35, pp. 631–633.

Toshiyuki Sawaguchi et al., "The Role of D1–Dopamine Receptor in Working Memory: Local Injections of Dopamine Antagonists Into the Prefrontal Cortex of Rhesus Monkeys Performing an Oculomotor Delayed–Response Task", Journal of Neurophysiology, Feb. 1994, pp. 515–528.

Andrew J. Saykin, PsyD. et al., "Neuropsychological Deficits in Neuroleptic Naïve Patients with First–episode Schizophrenia", Arch Gen Psychiatry, vol. 51, Feb. 1994, pp. 124–131.

Wolfram Schultz et al., "A Neural Substrate of Prediction and Reward", Science, vol. 275, Mar. 14, 1997, www.sciencemag.org, pp. 1593–1599.

James Seltzer, Ph.D. et al.,"Neuropsychological Rehabilitation in the Treatment of Schizophrenia", Connecticut Medicine, Sep. 1997, vol. 61, No. 9, pp. 597–608.

Theodore Van Putten, M.D. et al., "Plasma Homovanillic Acid as a Predictor of response to Fluphenazine Treatment", Psychopharmacology Bulletin, vol. 1, 1989, pp. 89–91.

Masataka Watanabe et al., "Increase of extracellular Dopamine in Primate Prefrontal Cortex During a Working Memory Task", © 1997 The American Physiological Society, pp. 2795–2797.

Bruce E. Wexler et al., "Normal neurocognitive performance after extended practice in Patients with schizophrenia", © 1997 Elsevier Science B. V., pp. 173–180.

Graham V. Williams et al., "Modulation of memory fields by dopamine D1 receptors in prefrontal cortex", Nature, vol. 376, Aug. 17, 1995, pp. 572–575.

Daniel S. O'Leary, Ph.D et al., "Auditory Attentional Deficits in patients with Schizophrenia—A Positron Emission Tomography Study", Arch Gen Psychiatry, vol. 53, Jul. 1996, pp. 633–641.

Dean F. Salisbury et al., "The N2 event–related potential reflects attention deficit in schizophrenia", Elsevier Science B.V., Biological Psychology 39, 1994, pp. 1–13.

Karen Shedlack et al., "Language processing and memory in ill and well siblings from multiplex families affected with schizophrenia", © 1997 Elsevier Science B.V., vol. 25, pp. 43–52.

Stanley V. Catts, M.D. et al., "Brain Potential Evidence for an Auditory Sensory Memory Deficit in Schizophrenia", Am J Psychiatry 152:2; Feb. 1995, pp. 213–219.

U. Schall et al., "A left temporal lobe impairment of auditory information processing in schizophrenia: an event–related potential study", © 1997 Elsevier Science Ireland Ltd., Neuroscience Letters 229, pp. 25–28.

Michael F. Green Ph.D. et al., "Backward Masking Performance in Unaffected Siblings of Schizophrenic Patients—Evidence for a Vulnerability Indicator", Arch Gen Psychiatry, vol. 54, May 1997, pp. 465–472.

Kristin S. Cadenhead et al., "The Relationship of Information–Processing Deficits and Clinical Symptoms in Schizotypal Personality Disorder", © 1996 Society of Biological Psychiatry, vol. 40, pp. 853–858.

Sören Nielzén et al., "Perceptual Grouping due to Pitch and Amplitude in Hallucinating Schizophrenics", Psychopathology 1997, vol. 30, pp. 140–148.

Lynn E. DeLisi et al., "Schizophrenia as a chronic active brain process: a study of progressive brain structural change subsequent to the onset of schizophrenia", © 1997 Elsevier Science Ireland Ltd., Nuroimaging Section 74, pp. 129–140.

Sandra S. Kindermann et al., "Review of functional magnetic resonance imaging in schizophrenia", © 1997 Elsevier Science B.V., Schizophrenia Research 27, pp. 143–156.

Steven M. Silverstein et al., "Reduced Top–Down Influence in Auditory Perceptual Organization in Schizophrenia", Journal of Abnormal Psychology 1996,. vol. 105, No. 4, pp. 663–667.

Schneider et al. "Self–Regulation of Slow Cortical Potentials in Psychiatric Patients: Schizophrenia," © Dec. 1992, Biofeedback and Self–Regulation, vol. 17, No. 4, pp. 277–292.

Tretter F., Perspectives of Computer–Aided Therapy and Rehabilitation in Psychiatry, Jul. 1996, pp. 475–486.

Frith, C., "The Role of the Prefrontal Cortex in Self–Consciousness: The Case of Auditory Hallucinations," pp. 1505–1512 (1996).

Nagarajan et al.., "Practice–Related Improvements in Somatosensory Interval Discrimination Are Temporally Specific But Generalize Across Skin Location, hemisphere, and Modality," The Journal of Neuroscience, Feb. 15, 1998, pp. 1559–1570.

Merzenich et al., "Temporal Processing Deficits of Language–Learning Impaired Children Ameliorated by Training," Science, vol. 271, pp. 77–81, Jan. 5, 1996.

Lederman, S. J. (1974). Tactile roughness of grooved surfaces: The touching process and effects of macro– and microsurface structure. Perception & Psychophysics, 16 (2), 385–395.

Vega–Bermudez, F., Johnson, K. O., & Hsiao, S. S. (Mar., 1991). Human Tactile Pattern Recognition: Active Versus Passive Touch, Velocity Effects, and Patterns of Confusion. Journal of Neurophysiology, 65 (3), 531–546.

Craig, J. C., & Rhodes, R. P. (1992). Instrumentation & Techniques, Measuring the error of localization. Behavior Research Methods, Instruments, & Computers, 24 (4), 511–514.

Evans, P. M., & Craig, J. C. (1992). Response competition: A major source of interference in a tactile identification task. Perception & Psychophysics, 51 (2), 199–206.

Evans, P. M., & Craig, J. C. and Rinker, M. A. (1992). Perceptual processing of adjacent and nonadjacent tactile nontargets. Perception & Psychophysics, 52 (5), 571–581.

Carey, L. M., Matyas, T. A., Ph.D., and Oke, L. E. MappSc. Sensory Loss in Stroke Patients: Effective Training of Tactile and Proprioceptive Discrimination. Archives of Physical Medicine and Rehabilitation, vol. 74, (Jun., 1993) pp. 602–611.

Craig, J. C. (1993). Anomalous sensations following prolonged tactile stimulation. Neuropsychologia, 31, (3), 277–291.

Dannenbaum, R. M., & Jones, L. A. (Apr.–Jun., 1993). The Assessment and Treatment of Patients who Have Sensory Loss Following Cortical Lesions. Journal of Hand Therapy, 130–138.

Vickery, R. M., Morley, J. W., & Rowe, M. J. (1993). The role of single touch domes in tactile perception. Experimental Brain Research, 93, 332–334.

Yekutiel, M., and Guttman, E. (1993). A Controlled trial of the retraining of the sensory function of the hand in stroke patients. Journal of Neurology, Neurosurgery, and Psychiatry, 56, 241–244.

Byl, N. N., Merzenich, M. M., & Jenkins, W. M.,. A primate genesis model of focal dystonia and repetitive strain injury: I. Learning–induced dedifferentiation of the representation of the hand in the primary somatosensory cortex in adult monkeys. American Academy of Neurology, 47, (Aug., 1996) 508–520.

Byl, N., Wilson, F., Merzenich, M., Melnick, M., Scott, P., Oakes, A., McKenzie, A., (Apr., 1996). Sensory Dysfunction Associated With Repetitive Strain Injuries of Tendinitis and Focal Hand Dystonia: A Comparative Study. JOSPT, 23, (4), 234–244.

Kramis, R., C., Roberts, W. J., & Gillette, R. G., (Oct., 1996). Non–nociceptive Aspects of Persistent Musculoskeletal Pain. JOSPT, 24, (4), 255–266.

Byl N. N., Merzenich, M. M., Cheung, S., Bedenbaugh, P., Nagarajan, S. S., & Jenkins, W. M., (Mar., 1997). A primate model for studying focal dystonia and repetitive strain injury: Effects on the primary somatosensory cortex. Physical Therapy, 77, (3), 269–284.

Patentec Search Report, Jun. 15, 1998.

Thomas Elbert et al., Alteration of digital representations in somatosensory cortex in focal hand dystonia, (Nov. 16, 1998), NeuroReport, vol. 9, No. 16, pp. 3571–3575.

Byl, Nancy, Ph.D., and Topp, Kimberly S. Ph.D., Focal Hand Dystonia, (Jan., 1998), Physical Therapy Case Reports, vol. 1, No. 1, pp. 39–52.

Bruno Kopp et al., Plasticity in the motor system related to therapy–induced improvement of movement after stroke, (Mar., 1999), NeuroReport, vol. 10, No. 4, pp. 807–810.

James J. DiCarlo et al., Structure of Receptive Fields in Area 3b of Primary Somatosensory Cortex in the Alert Monkey, (Apr. 1, 1998), The Journal of Neuroscience, pp. 2626–2645.

J.R. Phillips et al., Spatial pattern representation and transformation in monkey somatosensory cortex, (Feb., 1988), Proc. Natl. Acad. Sci., Neurobiology, vol. 85, pp. 1317–1321.

APPARATUS AND METHODS FOR TREATING MOTOR CONTROL AND SOMATOSENSORY PERCEPTION DEFICITS

RELATED APPLICATIONS

This application is a continuation-in-part of application Ser. No. 08/970,339 filed Nov. 14, 1997, which is incorporated herein by reference for all purposes.

BACKGROUND OF THE INVENTION

The present invention relates to improving somatosensory perception and motor control deficits. More particularly, the present invention relates to computer-implemented methods and apparatus for improving somatosensory perception and motor control in an individual via somatosensory training that incorporates proprioceptive, tactile and/or kinesthetic sensory input.

Motor control problems range from shaking in the hands and fingers to more severe issues such as debilitating pain related to a motor control deficit. Often, the motor control problems may include weakness, fatigue, motor control inaccuracy, loss of coordination, loss of voluntary movement, abnormal synhcracies of movement, involuntary dystonic movements, e.g., when a hand touches an object, and involuntary motor movement such as co-contraction of flexors and extensors when the hand touches a target surface. For some individuals, these abnormalities may compromise a person's ability to attend work, school or even handle personal care or common household tasks.

Motor control and somatosensory deficits in individuals find their genesis in a variety of different causes. Typical causes include injury, birthing, inflammation, cardiopulmonary malfunction, impingement, chronic pain, disease, aging, degeneration, atrophy and gradual "occupational" type injury. The deficits related to an injury may be associated with trauma, stroke, anoxia, aneurysm, embolism, invasive surgery, etc. The deficits may also be related to any peripheral or central nervous system deficit. Examples of diseases capable of inducing motor control and/or somatosensory deficits include meningitis, infections, allergy, diabetes, neuromuscular disorders, and cancer. Alternatively, some motor control and somatosensory problems may not be not caused by an acute injury or disease, but may be associated with a gradual degradation of the somatosensory or motor control system over time. Examples of progressive degradation of the somatosensory and/or motor control systems over time include work-induced focal dystonia, myaesthonia gravis, amyotrophic sclerosis, torticollis, Alzheimer's disease, cerebral palsy, multiple sclerosis and movement disorders such as Parkinson's disease, ataxia, Huntington's chorea, and other progressive neurological illnesses. In some cases, the cause of the motor control impairment may be unaccountable.

In particular, focal hand dystonia is the involuntary co-contraction of flexors and extensors in the hands when performing a target task. In other words, there is a loss of reflex inhibition leading to uncontrolled contraction of the flexors pulling the hand closed and the extensors pulling the digits open. As a result, the individual typically loses fine motor control of the hand and can no longer perform tasks that require fine motor coordination.

A common origin of focal dystonia is as a component of a repetitive use. Repetitive strain injuries may be the result of attended rapid movements repeated over a relatively long period of time. Generally, these potentially harmful rapid movements occur at a frequency at or below about 100 milliseconds. Typical symptoms of focal hand dystonia include pain, swelling, inflammation and muscle spasm, loss of motor control, and involuntary movements of the affected hand. Rest and anti-inflammatories can decrease the symptoms but continued repetition can lead to painful fatigue and awkward movements.

Individuals who frequently suffer from these motor control deficits include those who are highly skilled and required to repeatedly execute rapid motoric tasks. Conditions such as stress and high attention may also contribute to the development of the condition. For example, musicians and typists, or other skilled manual workers who are required to repeatedly execute rapid alternating movements (e.g., to produce trills and keyboard strokes or to perform a particular assembly line task) are particularly prone to motor control degradation of this nature. Potentially harmful rapid movements may also include rapid simultaneous movement of adjacent portions of a limb which can otherwise be controlled independently, e.g., when multiple digits of one hand are opened and closed rapidly.

Unlike traumatic injury patients, most repetitive strain injury subjects experience a slow onset of symptoms such as painful inflammatory problems of the capsule, ligaments, tendons and fascia. Subsequently, if the potentially harmful repetitive movements are continued, the degradation of motor control ultimately develops, primarily in the area responsible for the movement. Eventually, the dysfunction may spread to other parts of the body and other tasks, and the patient may then report a feeling of awkwardness, fatigue, or impaired timing or force.

In the past, evaluation and treatment of deficient motor skills typically required face-to-face treatment in a clinical setting with a health care professional. Unfortunately, the convenience or ability of the person to travel to the treatment site limits the treatment frequency and may compromise treatment efficacy. This limitation may be further exacerbated if the motor control deficit compromises the ability of the individual to travel to the treatment site. More importantly, treatment consistency and quality with conventional manual testing has been limited due to the reliance on estimated and non-quantitative judgements by the health care professional regarding treatment efficacy.

Historically, regardless of whether the deficit is accompanied by a loss of motor or sensory ability, the manual training may typically include strengthening, flexibility, splinting, conditioning and neuromuscular retraining techniques, and has produced limited success. This is partly because the conventional treatments tend to be directed at the symptoms but do not attempt to identify nor address the source of the problem. As a result, despite rest and conventional treatment, the motor control problems, and any accompanying issues such as inflammation, often return as soon as the subjects attempt to resume the repetitive movements.

In view of the foregoing, there are desired improved apparatus and methods for treating motor control deficits accompanied by sensory degradation.

SUMMARY OF THE INVENTION

The present invention describes computer-implemented methods and apparatus for treating somatosensory perception and motor control deficits. The somatosensory perception and motor control deficits may have their genesis in a wide variety of issues including injury, disease, and a gradual degeneration over time due to repetitive strain, for example. Typically, the motor control deficits are related to somatosensory feedback problems. By administering a computer-implemented training regime directed to improve somatosensory perception and motor control, abnormal motor control deficits may be substantially improved. The computer-implemented training regime includes somatosensory and motor control exercises which may be flexibly administered. The training regime may be directed to progressively improving one or more somatosensory perception abilities and/or motor control deficits.

The invention also encompasses several computer-implemented systems for training one or more somatosensory perception and motor control deficits. The systems generally consist of a computer and a testing apparatus. The computer typically has a processor, a storage means for storing unprocessed training information, processed training information and instructions for manipulating training information. Three testing apparatus are described which implement somatosensory perception and motor control exercises based on proprioceptive, kinesthetic and tactile perception. The testing apparatus may allow for user input, provide output to the user, and require for a wide range of sensory feedback and motor control ability from the person.

The invention relates in accordance with one embodiment to a somatosensory and motor control training device for improving one of a somatosensory perception deficit and a motor control deficit for a human subject. The device includes a plurality of force sensors situated in proximity such that each may receive one or more fingers from a hand of the human subject. The plurality of force sensors are capable of force feedback from the one or more fingers. The device also includes a processor in electrical communication with the plurality of force sensors.

The invention relates in accordance with another embodiment to a somatosensory perception and motor control training device for improving one of a somatosensory perception deficit and a motor control deficit for a human subject. The device includes a set of pins, wherein each pin is capable of independent vertical displacement. The device also includes a set of actuators coupled to the set of pins. The device further includes a processor in electrical communication with the set of actuators.

The invention relates in accordance with yet another embodiment to a somatosensory perception and motor control training device for improving one of a somatosensory perception deficit and a motor control deficit for a human subject. The device includes a probe capable of linear displacement. The device also includes an actuator coupled to the probe. The device also includes a sensor coupled to the probe. The device additionally includes a processor in electrical communication with the actuator and the sensor.

The training methods and apparatus described herein are capable of driving sensory and motoric improvements in temporal, spatial and intensity resolution of somatosensory feedback. In addition, the methods and apparatus allow the training to be monitored and adapted on a quantitative basis as treatment proceeds. Additionally, the invention relates to methods for training motor control deficits and computer software to modify the training. Advantageously, this provides an accurate and improved training tool for treating motor control deficits.

The training methods and apparatus also allow an individual to train one or more somatosensory and motor control problems at a site remote from a clinician and still be monitored by the clinician. For example, the computer-implemented methods and apparatus allow treatment to be administered in the convenience of the person's own home and on a daily basis if desired.

The present invention is applicable to address the motor control deficits associated with a large number of health care issues. For example, present invention is applicable to address the motor control deficits associated with chronic pain, work-induced focal dystonia, Alzheimer's disease, stroke, torticollis, cerebral palsy, multiple sclerosis, movement disorders in Parkinson's disease, Huntington's chorea, peripheral and spinal chord nerve injuries and regeneration, skin graphs, and other surgical repairs of the joint or soft tissues, as well as in other progressive neurological illnesses.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which.

DETAILED DESCRIPTION OF THE PREFERRED EMBODIMENTS

Figure 1:
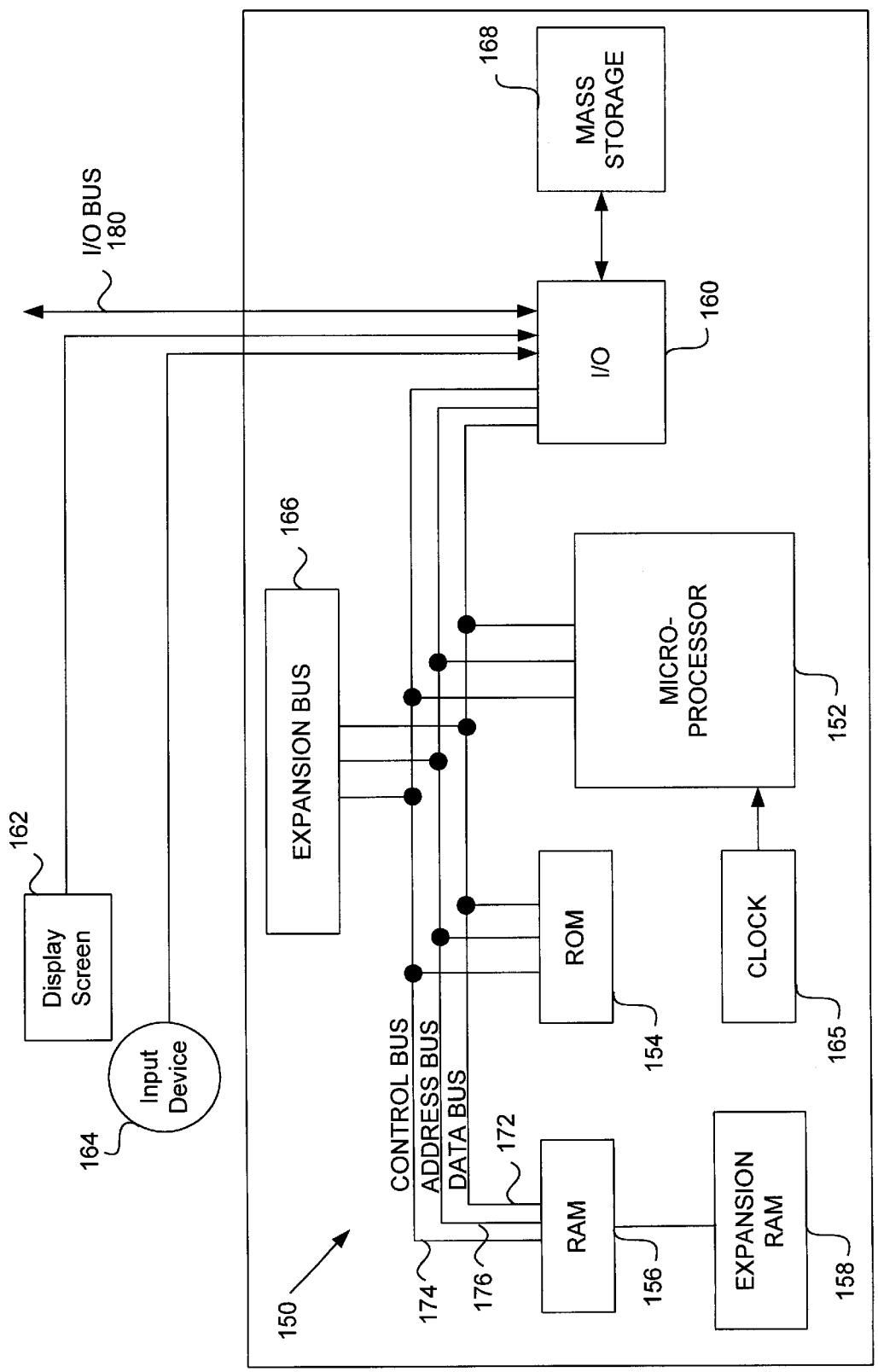
FIG. 1 shows a general-purpose computer system, representing a computer suitable for implementing the present inventive somatosensory perception and motor control deficit treatment methods.

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

The present invention describes computer-implemented methods and apparatus for treating motor control deficits. The motor control deficits may have their genesis in a wide variety of issues ranging from injury, biomechanical dysfunction, poor postural alignment, disease, or a gradual degradation of somatosensory and/or motor control over time due to repetitive use, for example. Typically, the motor control deficits are related to sensory feedback problems. By administering a computer-implemented training regime directed to improve sensory feedback and motor control, abnormal motor control deficits may be substantially improved. The computer-implemented training regime includes somatosensory and motor control exercises which may be flexibly administered. Several training apparatus are described for implementing the somatosensory and motor control exercises. The training apparatus described herein are capable of driving sensory and motoric improvements in temporal, spatial and intensity resolution of somatosensory feedback. In addition, the methods and apparatus allow the training to be monitored and adapted on a quantitative basis as treatment proceeds. Advantageously, this provides an accurate and improved training tool for treating somatosensory perception and motor control deficits. Further, the computer-implemented methods and apparatus allow treatment to be administered in the convenience of the person's own home and on a daily basis if desired.

A. Theory

For an individual suffering from motor control deficits, the disabling motor control problems are often accompanied or caused in part by sensory problems. Commonly, these sensory problems are not caused by a peripheral nerve injury or disease. Instead, these sensory problems may be related to a different health issue or prolonged degradation of the somatosensory control structures.

Broadly speaking, somatosensory inputs refer to feedback that encompasses muscle position, touch and/or movement. Somatosensory perception includes tactile perception, kinesthetic perception and proprioception. Tactile perception generally refers to sensing texture with the skin. Tactile sensing involves, for example, differentiation between rough and smooth stimulation as well as depth and temporal information, i.e. sliding one's finger across a surface to obtain texture. Proprioception and kinesthetic perception involve inputs from muscles, joints and skin contributing to movement control and locational sense respectively. More specifically, kinesthetic sensing refers to sensing of body parts when the part is in motion and includes, for example, perception of the location of an arm in space which may be provided by information from the tendons, muscles as well as stretch of the skin and joint receptors. In addition to sensing static joint position, proprioception refers to the degree of force exerted in the tendons, joints and muscles or to the tactile and pressure sensing receptors in the fingertips and muscles.

Somatosensory deficits may manifest themselves in a variety of symptoms. While some individuals with motor deficits in the hands appear to retain the ability to sense gross inputs, they are typically unable to differentiate information in the afflicted regions. A common example is a loss in sensory differentiation between fingers of the hands. More specifically, they may be able to differentiate light touch from deep touch, or sharp from dull pressure, pain from non-pain, hot from cold; however, they are generally unable to accurately interpret tactile cues through the skin, joints, muscle afferents or tendons relative to location in the finger and hands.

An exemplary motor control deficit having symptoms related to somatosensory degradation is focal hand dystonia. One suggested hypothesis for the genesis of focal hand dystonia is that the rapid stimulation by multiple inputs to the digits results in the near simultaneous stimulation of adjacent digits, leading to near simultaneous firing in the motor cortex and somatosensory cortex. As a result, the multineural activation is interpreted as the digit movement being synchronous by the afferent muscular system. For example, a command for activating two fingers separately is confused as activating the fingers simultaneously. To further worsen the situation, as the fingers are activated simultaneously with the misinterpreted signal, the ability to control them may even further diminish. For example, a person may begin to use two fingers at a slower speed to compensate for the faulty signal, and thus the problem begins to spiral as their ability to distinguish information between the two fingers becomes worse at slower and slower speeds and the person thus compensates to use the fingers at yet even slower speeds. The practice at slower speeds may also become learned, interfering further in the ability to perform rapid movements.

While not wishing to be bound by theory, it is believed that repetitive delivery of substantially similar or nearly simultaneous afferent sensory inputs results in an integration of the representation of otherwise differentiable sensory input, thereby degrading the sensory feedback loop necessary for normal motor control. Hence, the progressive destruction of the otherwise highly differentiable representations of digit skin and of muscle afferent inputs involved with the muscles is believed to be one of the causes of the degradation of movement control, particularly in the hands and fingers. In other words, what started out as a degradation of the sensory feedback capability essential for proper motor control, eventually manifests over time as a motor control problem.

Correspondingly, it is believed by training an individual to differentiate substantially similar or nearly simultaneous afferent sensory inputs independently, the motor control deficits related to somatosensory control and processing deficits may be remediated, improved or at least halted. The training may be directed towards improvements in the temporal, spatial and intensity resolution of somatosensory feedback. By way of example, the individual may be trained to differentiate temporal information from a single finger with improved speed. Alternatively the individual may be trained to differentiate spatial information independently from multiple fingers.

B. General Philosophy of the Inventive Technique

Thus, in one embodiment of the present invention, an individual is engaged in a training regime that includes a set of interactive computer-implemented training exercises designed to facilitate and potentially maximize changes in the somatosensory control system that are attributable to motor control deficits. The training is typically directed towards differentiating feedback within the motor control system at progressively improving levels. More specifically, the exercises may focus on the ability to process higher definition and precision of motor control information, or to increase the amount, quality and clarity of information that is being used to make a motoric decision. To elaborate further, as the representation of information, and corresponding differentiation during processing, for a hand may range from being relatively simple to quite complex, the training may be directed towards increasing the amount of information, and differentiation therein, for tests involving the hands. By way of example, the training may require increasing information based on fine movement of the fingers as opposed to gross feedback from the palm.

Preferably, the interactive somatosensory and motor control exercises (those that use motor skills) are designed to be sufficiently intensive, both in repetition and exercise difficulty, such that lasting changes in the motor and sensory ability are achieved.

To implement the training regime, a number of somatosensory and motor control training devices are described. The training devices are capable of varying the temporal, spatial and intensity resolution of exercises to drive improvements in somatosensory input differentiation for an individual. Feedback may be obtained from the individual by the devices on a quantitative basis which allows for an accurate monitor of training progress and efficacy. The feedback may also be used to provide a basis for quantitative adaptations of exercise parameters to vary training difficulty. As the somatosensory perception and motor control training devices are used in conjunction with a computer, this allows the devices to be flexible in their implementation, as will be described below.

Accordingly, the training regimen and somatosensory perception and motor control training devices of the present invention differentially stimulate the affected regions of the individual. The stimulation may be with respect to tactile, proprioceptive and/or kinesthetic perception. Feedback from the individual may indicate the degree of difficulty or success the individual has in sensing differentially between the inputs. The stimulation is then adapted to the individual based on the feedback. In one aspect, the training is directed to isolating the sensory feedback from multiple locations. For example, training may require the individual to differentiate feedback between two fingers. Alternatively, the training may be directed to improving the output of the somatosensory perception and motor control system. Further, the training may be directed to improving the temporal precision of motor output.

The proposed apparatus and methods may be directed to drive improvements in differentiation which are attributable to the sensory deficiencies believed to be responsible for focal dystonia. In one aspect, the training is directed to relaxing the muscles responsible for the co-contraction of an opposing motor group. For example, this may be done by forcing a finger to perform a controlled motion using only one muscle in the opposing motor group.

The proposed training methods and apparatus are applicable to any treatment program geared to improving somatosensory perception and motor control deficits and is not necessarily limited to a movement disorder such as focal hand dystonia. By way of example, training with the present invention may also be applied to individuals who suffer motor losses as a result of stroke, a head, neck or spine injury. More specifically, as motor control deficits within stroke victims may be related to deficits in the motor cortex, the somatosensory cortex, or in the interaction between the two, training may be directed to improving processing in these areas. Thus, stroke victims may be trained to re-learn sensory and motor control in the areas affected by the stroke. This is in contrast to conventional approaches for training stroke victims wherein training is directed to strengthening the muscular system and neuromuscular education to try to improve voluntary control.

Training with the proposed training methods and apparatus may also be applied to individuals who suffer from other damage to the somatosensory perception and motor control system, i.e. a peripheral nerve entrapment. More specifically, the present invention is applicable to alleviating symptoms of pain and awkward hand movements due to weakness and carpal tunnel syndrome. In addition, in cases where an individual is compensating for the pain from the carpal tunnel syndrome and is posturing the hands to avoid the pain such that co-contraction results, the proposed methods and apparatus may be directed to alleviating the underlying motor control and sensory deficits to alleviate the pain.

Obviously, the treatment may be directed to drive improvements in more than one of the above mentioned cases. As the particular symptoms and deficits involved in a single or multiple motor control deficit may vary considerably between individuals, the training may thus flexibly involve a number of the above directions, simultaneously or at varying times, as desired for a particular individual.

The training is preferably progressive. Progressive training refers to increasing the level of difficulty of the exercises to reflect the improving abilities of the individual as training proceeds. By way of example, training may be directed to improving differentiation of force feedback, progressively requiring the individual to discriminate forces at continuously improved levels.

C. Exemplary Implementations

The features and advantages of these aspects of the invention, as well as other aspects of the present invention, may be better understood with reference to the figures and discussions that follow. As mentioned earlier, the motor control deficit remediation exercises of the present invention are preferably implemented using computer-based apparatus.

FIG. 1 illustrates, in accordance with one embodiment of the invention, an exemplary computer-controlled apparatus, including computer 150, for delivering computer-controlled stimuli to assess a subject for motor control deficits as well as to train a subject to remediate motor control deficits. As the terms are employed herein, assessment refers generally to ascertaining a test subject's risk for developing a motor control deficit or the subject's degree of affliction if there has already been onset. Training on the other hand may be applied to subjects who have already exhibited observable motor control deficits.

Referring to FIG. 1, a computer system 150 in accordance with the present invention includes a central processing unit (CPU) 152, read only memory (ROM) 154, random access memory (RAM) 156, expansion RAM 158, input/output (I/O) circuitry 160, display assembly 162, input device 164, and expansion bus 166. Computer system 150 may also optionally include a mass storage unit 168 such as a disk drive unit or nonvolatile memory such as flash memory and a real-time clock 165. In one embodiment, mass storage unit 168 may include units which utilize removable computer readable media, such as floppy disks, opto-magnetic media, optical media, and the like for the storage of programs and data.

CPU 152 is preferably a commercially available, single chip microprocessor such as one of the Intel X86 (including Pentium™ or Pentium™) or Motorola 680XX family of chips, a reduced instruction set computer (RISC) chip such as the PowerPC™ microprocessor available from Motorola, Inc., or any other suitable processor. CPU 152 is coupled to ROM 154 by a data bus 172, control bus 174, and address bus 176. ROM 154 may partially contain the basic operating system for the computer system 150. CPU 152 is also connected to RAM 156 by busses 172, 174, and 176 to permit the use of RAM 156 as scratch pad memory. Expansion RAM 158 is optionally coupled to RAM 156 for use by CPU 152. CPU 152 is also coupled to the I/O circuitry 160 by data bus 172, control bus 174, and address bus 176 to permit data transfers with peripheral devices.

I/O circuitry 160 typically includes a number of latches, registers and direct memory access (DMA) controllers. The purpose of I/O circuitry 160 is to provide an interface between CPU 152 and such peripheral devices as display assembly 162, input device 164, mass storage 168, and/or any other I/O devices. I/O circuitry 160 may also include analog-to-digital (A/D) converters, digital-to-analog (D/A) converters, as well as other control circuits for controlling and receiving feedback data from the I/O devices. The I/O devices suitable for generating stimuli to be administered to the test subject and for receiving responses therefrom may be coupled to I/O bus 180 of computer 150. Display assembly 162 of computer system 150 is an output device for displaying objects and other visual representations of data, as well as for generating visual stimuli in one embodiment.

The screen for display assembly 162 can be a device that uses a cathode-ray tube (CRT), liquid crystal display (LCD), or the like, of the types commercially available from a variety of manufacturers. Input device 164 can be a keyboard, a mouse, a stylus working in cooperation with a position-sensing display, or the like. Alternatively, input device 164 can be an embedded RF digitizer activated by an "active" RF stylus. As a further alternative, input device 164 may be any type of switch capable of communicating a test subject's response to computer system 150. Therefore, as used herein, the term input device will refer to any mechanism or device for entering data and/or pointing to a particular location on a screen of a computer display. One or more input devices may be provided to control computer 150 and/or to receive responses from the test subject. The aforementioned input devices are available from a variety of vendors and are well known in the art.

Some type of mass storage 168 is generally considered desirable. However, mass storage 168 can be eliminated by providing a sufficient amount of RAM 156 and expansion RAM 158 to store user application programs and data. In that case, RAMs 156 and 158 can optionally be provided with a backup battery to prevent the loss of data even when computer system 150 is turned off. However, it is generally desirable to have some type of long term mass storage 168 such as a commercially available hard disk drive, nonvolatile memory such as flash memory, battery backed RAM, PC-data cards, or the like.

In operation, computer system 150 is employed to generate control signals to the stimuli generator(s) to produce the stimuli of the various tests. These stimuli are then furnished to the test subject for assessment and/or training, and the responses from the test subject may then be recorded by input device 164 (or another suitable input device) and analyzed by CPU 152. If desired, feedback (both positive and negative with emphasis preferably on the positive) to the test subject may be given at various stages of the test(s) via, for example, display assembly 162.

It should be borne in mind that although computer system 150 is discussed in some detail herein to facilitate discussion, the invention itself may be practiced using a variety of suitable computer-implemented techniques. In general, any suitable computer system may be employed for generating control signals to the stimuli generators and receive feedback from the input device(s). Further, the inventive training technique disclosed herein may be implemented via a computer network, such as a local area network (LAN), wide area network (WAN) or a global computer network such as the Internet (also popularly known as "the Web"). In the latter cases, the inventive computer-implemented assessment and/or training technique may be implemented at least in part as downloadable computer software and/or data (e.g., applets such as JAVA™ applets from Sun Microsystems Inc.). The downloadable computer software and data may be kept on one or more servers on the network, accessible by any client computer or terminal capable and authorized for such access (via, for example, a web browser). The client computer/terminal may then be employed to control an appropriate stimuli generator and to gather responses from the test subject. To facilitate testing, the downloadable computer software and data can be downloaded once and reused over and over at the client computer/terminal. Alternatively, the downloadable computer software and data can be downloaded for each individual testing session via the network as needed. In some cases, the computer software may be executed at the servers themselves, with program outputs transmitted to the client computer/terminal for interfacing with the I/O devices. Alternatively, execution may take place locally at the client computer/terminal after downloading. Data pertaining to the client's responses may be transmitted to another computer on the network to permit a remote health care professional to monitor the patient's participation and progress simultaneously or on a periodic basis. Network computing techniques and implementations therefore are well known in the art and are not discussed in great detail here for brevity's sake.

Figure 2:
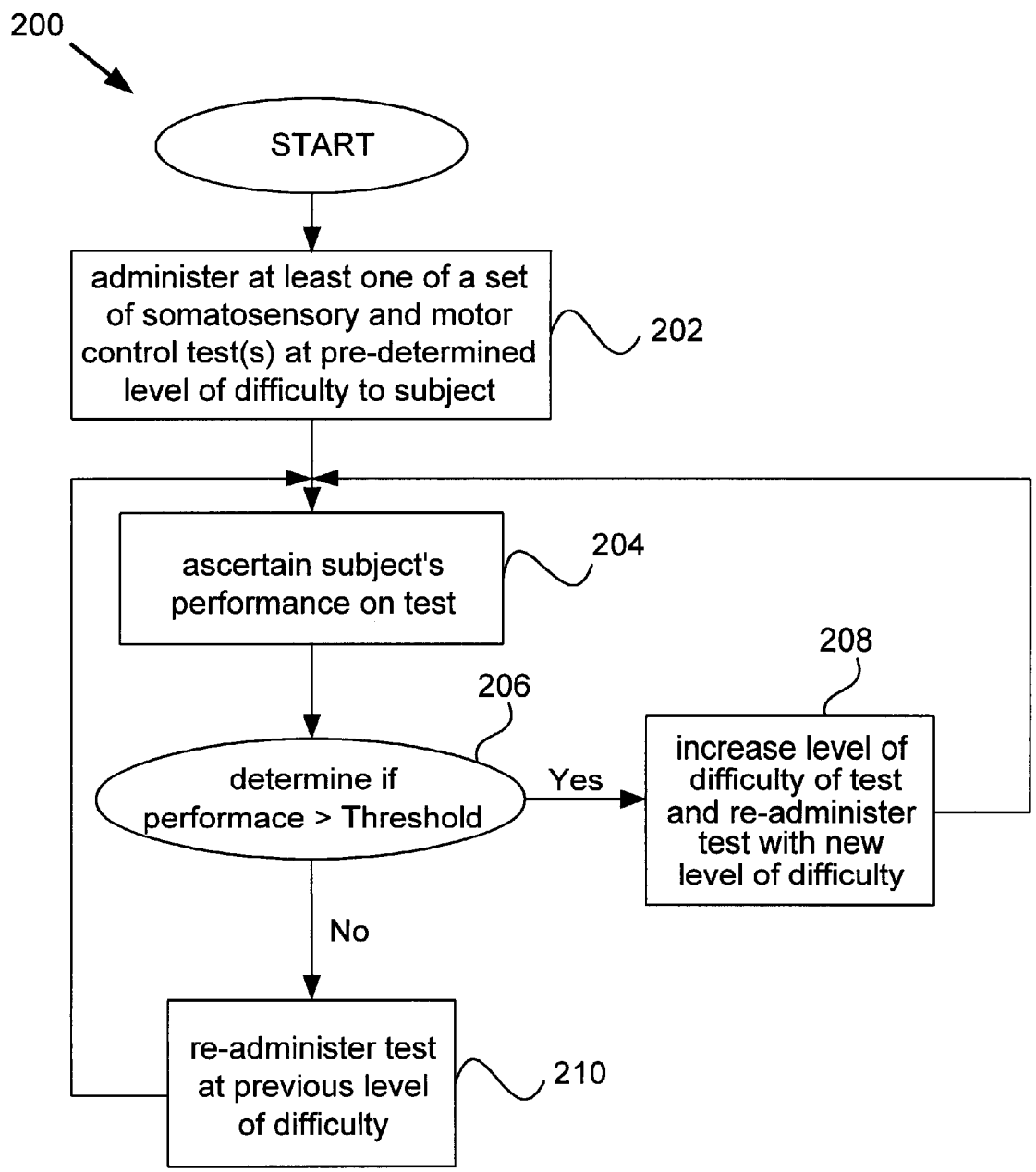
FIG. 2 illustrates a general computer-implemented method for treating a person with one or more somatosensory perception and motor control deficits, in accordance with one embodiment of the present invention.

FIG. 2 illustrates, in accordance with one embodiment of the present invention, a general computer-implemented method 200 for treating a person with one or more somatosensory perception and motor control deficits. The method 200 generally begins with administering a set of somatosensory and motor control exercises at a predetermined level of difficulty (202). By way of example, the predetermined level of difficulty may correspond to the performance expected of an individual of whose motor control deficits are sufficient for treatment. The person's performance from the test is then ascertained (204) using the computer-implemented apparatus. The performance is then compared to a predefined performance threshold (206). The predefined threshold may be, for example, the performance expected of an individual of whose motor control deficits are sufficient for treatment. Alternatively, the predefined benchmark may correspond to the motor control performance expected of an individual having normal motor control abilities. Obviously, the benchmark applied may depend on the nature of the exercises administered and the particular motor control deficit being trained.

If the performance is above the predefined performance threshold (208), then the level of difficulty of the training may be increased and the testing may be readministered (202). To increase the level of difficulty of the test, the parameters for the current exercises may be adapted. The parameters to be adapted may include the temporal, spatial or intensity parameters of the exercise, which will depend on the particular exercise and be discussed below with respect to FIGS. 3–5. Alternatively, one or more of the exercises may be added or removed to vary testing difficulty.

If the score of the test is not above the predefined performance threshold (210), then the previous exercises may be readministered at the current level of difficulty (202). Alternatively, if the person fails to perform successfully after a given number of repetitions (e.g. 2 or 3), the level of difficulty may be lowered.

It should be noted that the general computer-implemented method 200 may be administered at an administration site or preferably using a remote computer (i.e. local to the human subject). This is advantageous over the prior art in which testing at an administration site may limit the convenience or ability of the person to travel to the treatment site and may thus compromise treatment efficacy. The remote computer is preferably within the user's home and may be implemented via a computer network such as a wide area network (WAN) or the Internet.

Preferably, the exercises are adapted responsive to the performance of the individual. In this manner, the exercises are kept suitably challenging to drive progressive motoric improvements. In one example, the subjects operate on a on a 3-up, 1-down staircase or other learning progression designed to assure that the exercises maintain a level of difficulty proximate to the adapting motor control abilities of the individual. More specifically, when they get three "answers" correct in a row, the task becomes more difficult by one small difficulty step; while when they get one "answer" incorrect, the task becomes easier, by one difficulty step or more. Preferably, the adapting the parameters becomes easier by a larger backward than forward difficulty step to facilitate lasting changes of piecewise improvements. In one embodiment, the exercises are preferably adapted automatically by the computer to facilitate remote implementation of the training. For example, as testing difficulty may include response time, the computer may be used to automatically adapt the required response time as the subject improves in accuracy and performance time.

FIGS. 3 through 5 illustrate exemplary training apparatus, methods and exercises suitable for implementing the motor control directions outlined above. As the terms are employed herein, an exercise is referred to as a task when the subject is required to execute a motor function. Further, an exercise is referred to as a test when the subject's performance is monitored in the exercise, either with or without the subject's awareness.

Figure 3A:
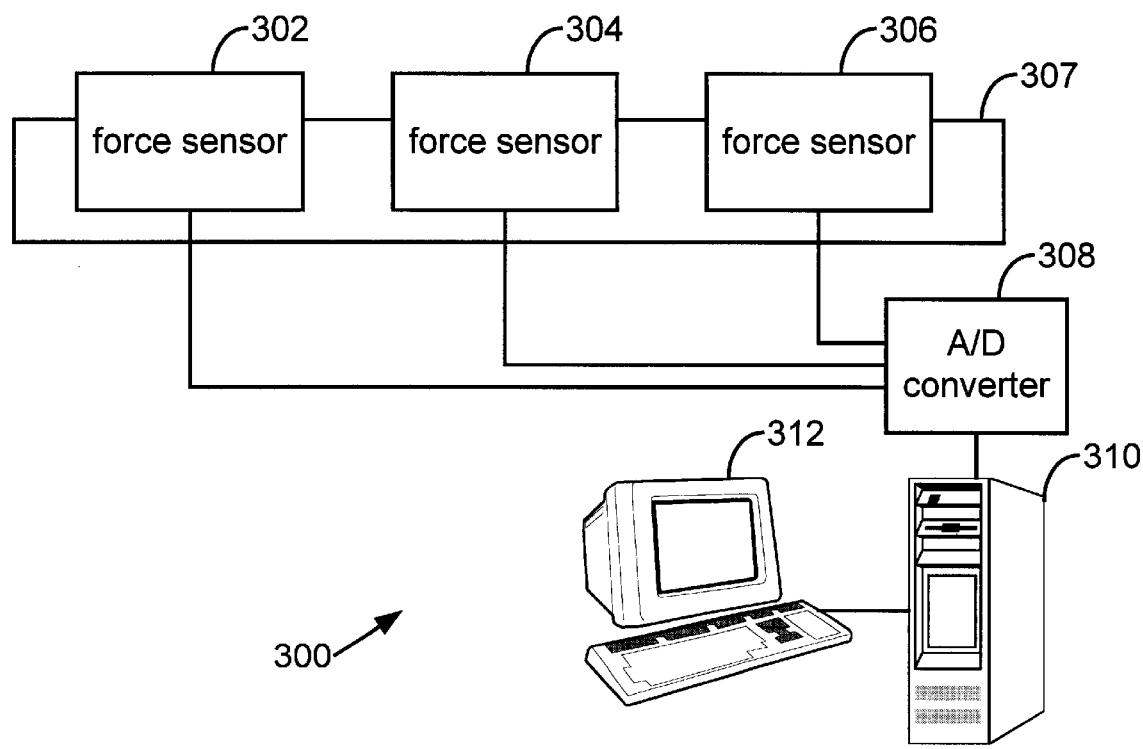
FIG. 3A illustrates a force sensitive system capable of driving somatosensory perception and motor control improvements in a human subject in accordance with one embodiment of the present invention.

FIG. 3A illustrates a force sensitive system 300 capable of driving somatosensory and motor control improvements in a human subject. In particular, the force sensitive system 300 is suitable for driving proprioceptive improvements in a human subject. The force sensitive system 300 includes three force sensors 302, 304 and 306. The force sensors 302, 304 and 306 are each capable of linear motion and sensing a force applied by a finger. Typically, the force sensors 302, 304 and 306 are situated upon a base 307 in proximity to each other such that they may accommodate a user's hand. The force applied to the force sensors 302, 304 and 306 is then converted to a digital signal in an A/D converter 308 to be processed by a computer 310. The computer 310 may be any suitable processing apparatus such as that described with respect to FIG. 1. Supplementary I/O interfaces may also be present as one skilled in the art would appreciate and those described with respect to FIG. 1 are sufficient to facilitate processing between the computer 310 and the force sensors 302, 304 and 306.

To facilitate user interface, the computer 310, or another computer, may be used to present training information visually or auditorally using peripheral devices, i.e., with a monitor 312. Typically, a software program running on the computer 310 issues instructions for an exercise and may display visual feedback of the user's performance in the exercise. In one embodiment, the software program may include computer-implemented animations and entertainment methods. Preferably, the exercises may be designed to induce a high level of engagement for the human subject.

Figure 3B:
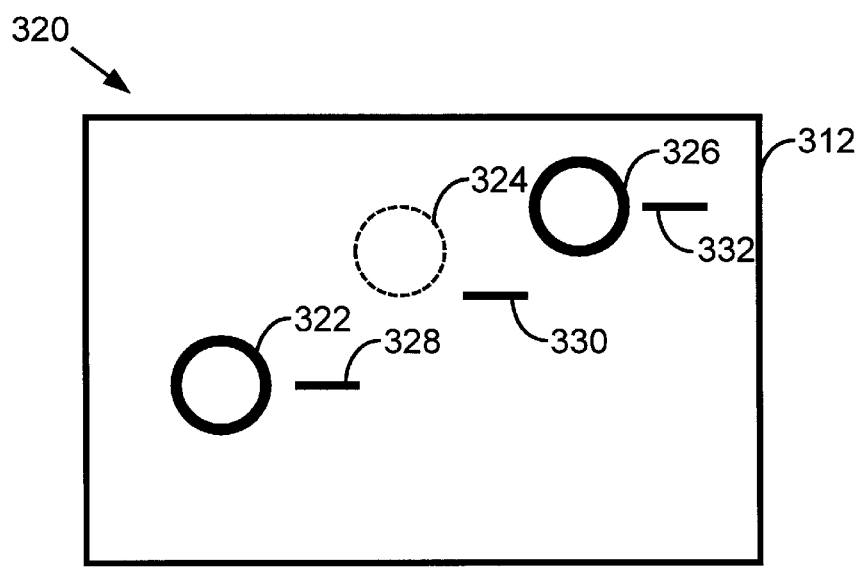
FIG. 3B illustrates a ball positioning exercise suitable for training somatosensory perception and motor control improvements using the force sensitive system of FIG. 3A.

FIG. 3B illustrates a ball positioning exercise 320 suitable for training somatosensory perception and motor control improvements using the force sensitive system 300. The ball positioning exercise 320 is visually presented on the monitor 312 and provides visual feedback to the user in the form of balls 322, 324 and 326 whose vertical position varies with the force applied to the force sensors 302, 304 and 306 respectively. In other words, as the individual pushes one of the force sensors 302, 304 and 306, the corresponding ball moves proportionally on the monitor 312.

In one suitable proprioceptive exercise, the individual is engaged in a test which requires the individual to move the ball 322 to a target height 328 on the monitor 312, thus requiring a controlled use of force from a finger. Alternatively, in a more difficult exercise, the target height 328 may move and the individual is required to track the position of the moving target height 328. In another suitable test, the individual is prompted to supply a first force using a first finger relative to the force of a second finger on a second of the force sensors 302, 304 and 306. In this case, the software program may supply information as to what forces to apply as well as feedback as to whether the correct force (within a predefined tolerance) is applied.

Alternatively, the testing may require the individual to correctly establish the position of multiple balls simultaneously or in a sequence. As illustrated in FIG. 3B, target heights 328, 330 and 332 may be illustrated as targets for the position of each of the balls 322, 324 and 326 respectively. In a more difficult version of multiple finger testing, the ball 324 may be invisible and the user must position it proximate to the visible target 330 based on the displayed target heights 328 and 332 as well as the forces applied to the force sensors 302 and 306. In other words, the individual must position the ball 326 to a specific point on the screen using the proprioceptive feedback of the other two fingers as well as estimated control of the third finger. When the individual believes the invisible ball is in the correct location, they may signal this in a suitable manner, i.e. by pressing a keyboard or mouse button. As testing proceeds, the target heights 328, 330 and 332 may all be varied, thus driving improvements in information differentiation for particular a finger or fingers for various force ranges.

To adapt the testing to facilitate further improvement, a number of parameters may be varied. Testing may be adapted by varying the amount of applied force required. Typically, increasing the force reduces the level of difficulty in the test. Alternatively, reducing the tolerance for a correct response may be used to increase the testing difficulty. By way of example, if the individual is required to respond with 100 grams of force, the task may be made more difficult by reducing the tolerance for a correct response from 50 grams of force to 25 grams of force. Subsequently, the tolerance may be reduced from 25 grams of force to 10 grams of force to make testing even more difficult. Further, the training may progress with the same exercises, or alternate exercises, to a correct tolerance response of 5 grams of force. Testing may also be adapted by varying the number of fingers in the response. For example, testing may be made more difficult by increasing the number of fingers in the testing. Preferably, the test 320 uses a minimum of two fingers.

Alternatively, testing may be adapted by the type and quality of feedback provided to the user. For example, in a testing game where the user must follow a bouncing ball on the monitor 312 with the appropriate force on the force sensor 304, the temporal parameters of following the ball may be altered. Alternatively, the time limit to complete the test may be adapted to vary testing difficulty. Typically, decreasing the response time increases the level of difficulty in the test.

Figure 3C:
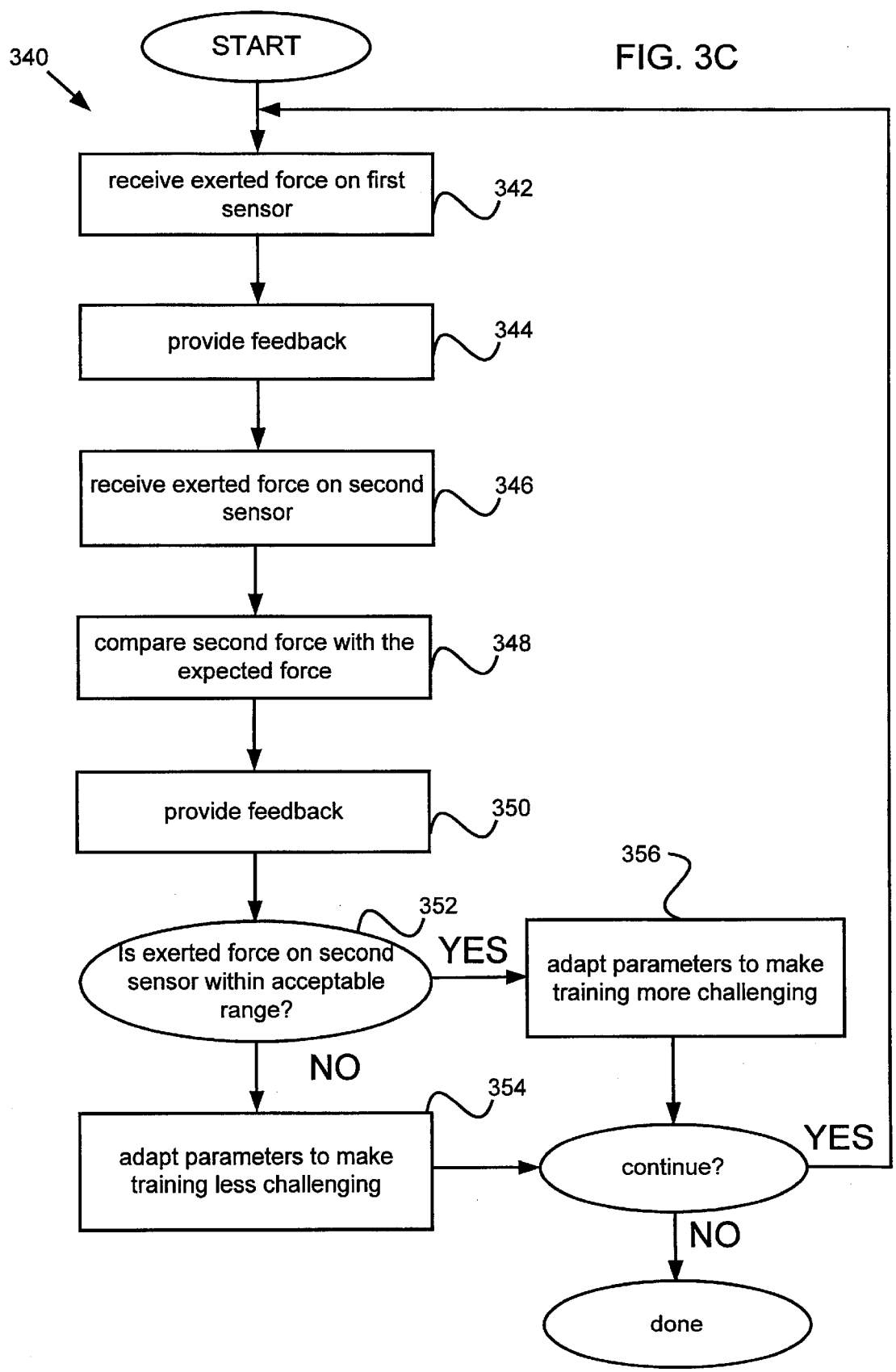
FIG. 3C illustrates a process of training a human subject with the force sensitive system of FIG. 3A in accordance with one embodiment of the present invention.

FIG. 3C illustrates a process 340 of training a human subject with the force sensitive system 300 in accordance with one embodiment of the present invention. The process 340 typically begins with receiving an exerted force (342) on one of the force sensors 302, 304 or 306 by an individual engaged in a game or a particular exercise. By way of example, the exercise may comprise positioning the balls 322 and 326 using two of the force sensors 304 and 306. The force received from the force sensor 304 may be compared to the target height 330 or an expected force for the exercise. Feedback is then provided to the subject (344), i.e. visually. For example, the feedback may be based on the difference between the exerted force and the expected force for the particular task.

At the same time or subsequently, the force from a second finger is received (346) on the force sensor 304. In one particular exercise, the user is required to provide a force on the force sensor 304 proportional to the force on the force sensor 302. By way of example, the force on the force sensor 304 must be half of that applied on the force sensor 302. The force received from the second sensor is then compared by the computer 310 to the expected force based on the test (348). For this test, feedback is then provided to the user when they indicate completion of the test (350).

To facilitate continuous training, it is determined whether the second force is within an acceptable tolerance for the test (352). If the force is suitable, the parameters for the testing may be adapted to make the training more challenging and training may proceed, if desired. If the force is not within the desired tolerance, the parameters for the testing may be adapted to make the training less difficult (354) and training may proceed, if desired. In one embodiment of the present invention, the force sensitive system 300 is present in the user's home or other convenient location and a networked remote computer is used to administer the training. By remote testing in this manner, the practical inconveniences of prior art testing techniques are advantageously avoided.

Having briefly explained some exemplary exercises and testing methods suitable for the force sensitive system 300, some preferable modifications for the force sensitive system 300 and other alternatives will now be described.

In another exercise using the force sensitive system 300, the force exerted on two of the three force sensors 302, 304 and 306 may be used to drive orthogonal movement of an object on the monitor 312. In this case, displacement of the object in the orthogonal directions is proportional to the force exerted on the force sensors. For example, the object may begin in the bottom left corner of the screen and a test may include moving the object to a particular point on the screen. Alternatively, the testing may be varied by adapting the requirements of the exercise. By way of example, a difficult exercise may be to move the object to draw a straight line. An even further difficult test would be to move the object to draw a circle.

Other temporal tests with a temporal component for the force sensitive system 300 may include the presentation of auditory information. In this case, the individual is provided with a series of auditory cues in which the frequency of each cue corresponds to a particular force sensor. The duration, sequence and intensity of the auditory cues would have to matched by corresponding input from the respective force sensor 302, 304 and 306.

Various alterations to the force sensitive system 300 may be implemented to permit testing alternatives. For example, the force sensitive system 300 is also capable of administering exercises based on tactile information. By way of example, the force sensitive system 300 may be adapted to present tactile information by applying a tactile material on the surface of the force sensors 302, 304 and 306. For example, a rough or rugose material may be used to enhance tactile perception. In this manner, the individual is now receiving proprioceptive feedback (how hard they are pushing) as well as tactile feedback (the degree of embedding of the material in the skin).

In another embodiment, the compliance of the force sensors 302, 304 or 306 may be altered to vary the force required to produce the desired motion or effect. As a result, the force the individual must apply to a force sensor may vary with consistent visual presentation. However, it is important to note that the sensory feedback for the finger in this case remains consistent. In other words, the individual is forced to use somatosensory feedback since the motor control required to produce the force using visual feedback for the variably compliant force sensors may be inconsistent. In one embodiment, the variable compliance is provided by a foam applied to the surface of the force sensors 302, 304 or 306. In this case, the person must apply greater motor action to apply equal immediate force to the force sensor, thus requiring increased control. Correspondingly, the compliance may be varied for the force sensors 302, 304 or 306 between tests to maintain a high level of engagement for the user.

In order to relieve strain on the finger due to continuous use, the surface of the force sensors 302, 304 or 306 may include a strain relief material, i.e. a foam or compliance spring. Obviously, the start point of the forces will vary with the compliance of the any material added to the top surface. In addition, a variety of materials may be applied to the surface of the force sensors to vary or enhance tactile and proprioceptive information.

Figure 4A:
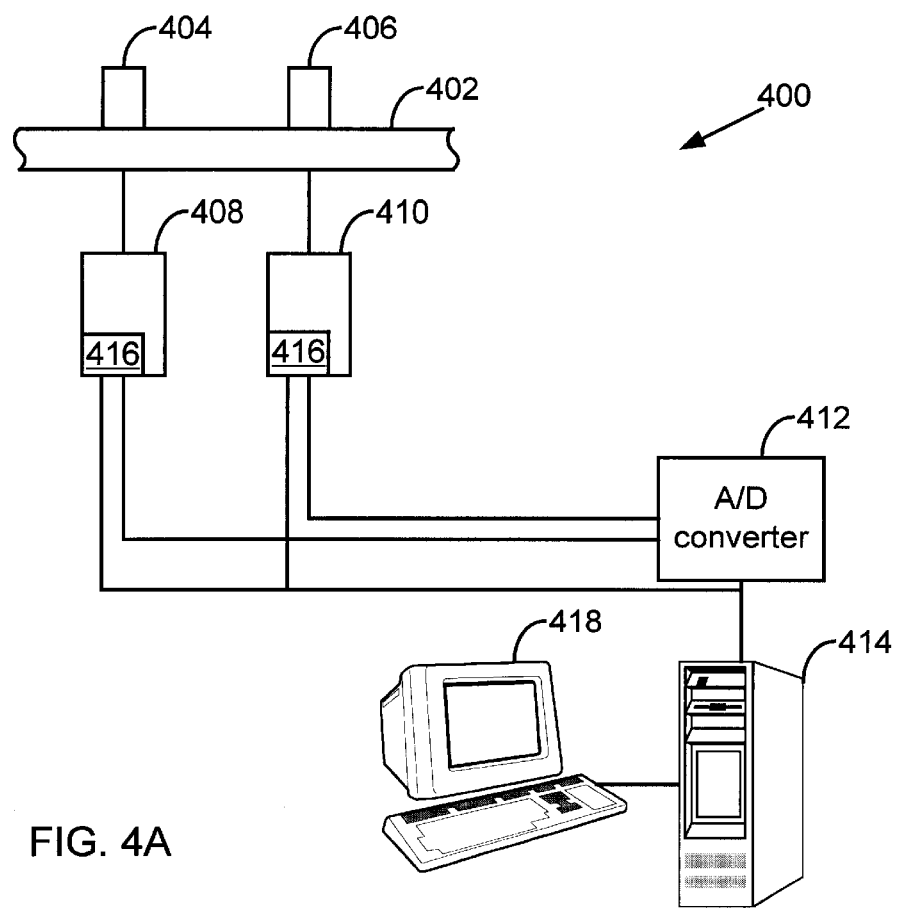
FIG. 4A illustrates a tactile testing apparatus capable of driving somatosensory perception and motor control improvements in a human subject in accordance with one embodiment of the present invention.
Figure 4B:
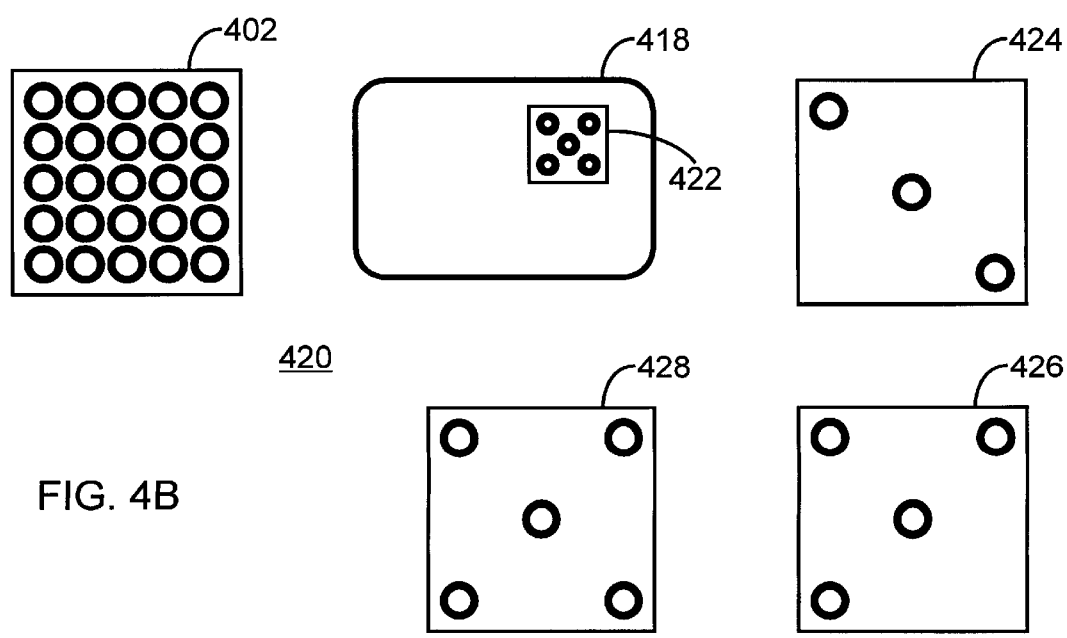
FIG. 4B illustrates a tactile recognition test suitable for training somatosensory perception and motor control improvements using the tactile testing apparatus of FIG. 4A.
Figure 4C:
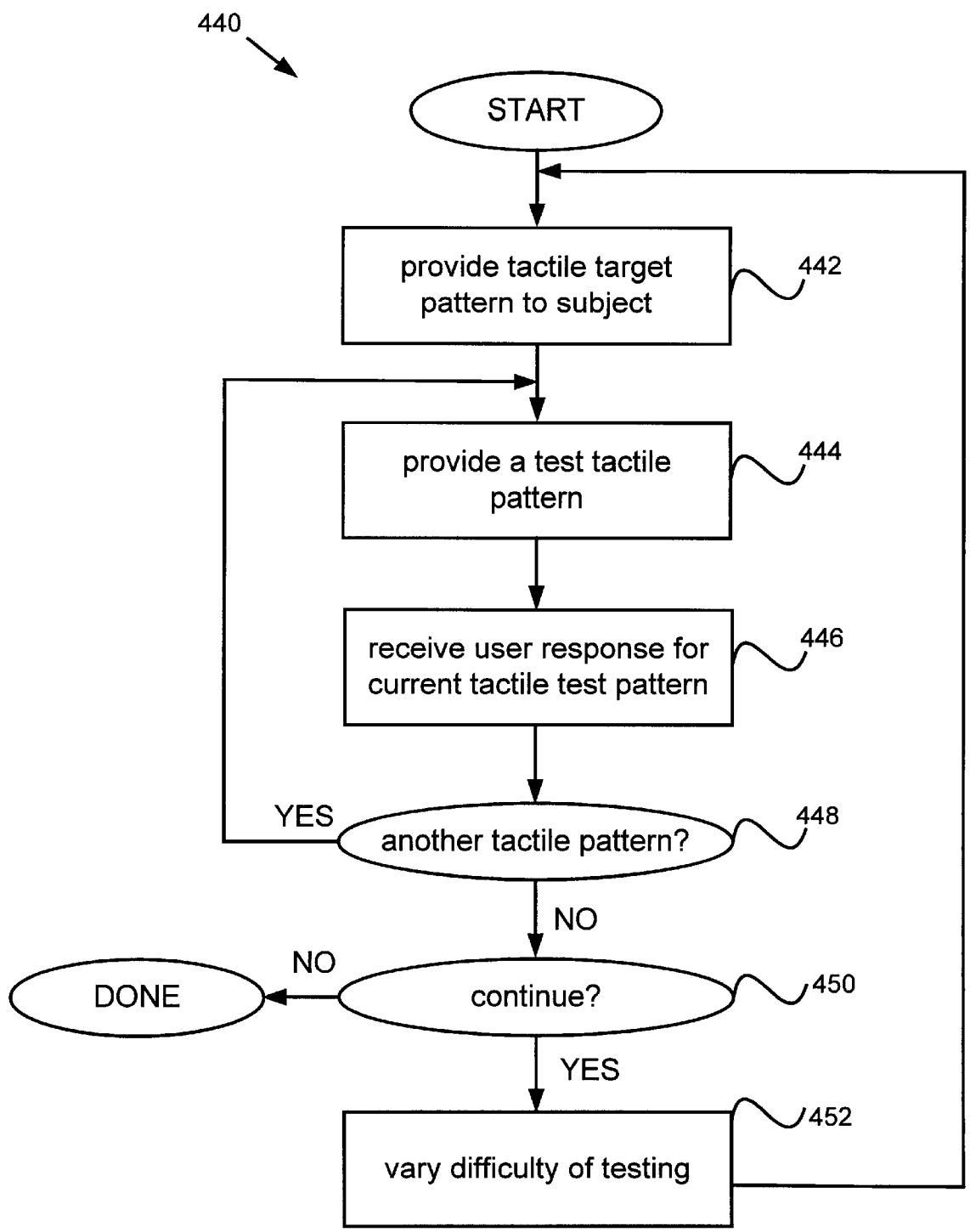
FIG. 4C illustrates a process of training a human subject with the tactile testing apparatus of FIG. 4A in accordance with one embodiment of the present invention.

FIG. 4A illustrates a tactile testing apparatus 400 capable of driving somatosensory perception and motor control improvements in a human subject. In particular, the tactile testing apparatus 400 is suitable for driving spatial, temporal and/or intensity improvements in the differentiation of tactile information in a human subject. The tactile testing apparatus 400 includes a tactile interface 402. The tactile interface 402 includes two spatially separated pins 404 and 406, whose height may be independently controlled for providing variable tactile information to an individual. The spatially separated pins 404 and 406 may be included in a larger set of spatially separated pins for the tactile interface 402. As illustrated in FIG. 4C, the tactile interface 402 may include a substantially rectangular five-by-five array of spatially separated pins.

Solenoids 408 and 410 are provided to move the spatially separated pins 404 and 406 respectively. The solenoids 408 and 410 receive input from an D/A converter 412, which communicates with a computer 414. A mechanical latching circuit 416 is also included in the solenoids such that continuous current does not have to be run through them. By way of example, the mechanical latching circuit 416 may be a permanent magnet. Again, supplementary I/O interfaces may also be present as one skilled in the art would appreciate and those described with respect to FIG. 1 are sufficient to facilitate processing between the computer 414 and the remainder of the tactile testing apparatus 400.

Similar to the force sensitive system 300, the computer 414 is responsible for implementing software for training with the tactile testing apparatus 400. By way of example, FIG. 4B illustrates a tactile recognition test 420 suitable for training somatosensory perception and motor control improvements using the tactile testing apparatus 400. In the tactile recognition test 420, the subject must identify a visual target pattern 422 on the monitor 418 which corresponds to the target tactile pattern 428 presented on the tactile interface 402, or vice versa.

Testing may include variations in the presentation of tactile patterns using the tactile interface 402. In one test, one or more foil tactile patterns, such as foil tactile pattern 424, may be presented with the target tactile pattern 428 in series of tactile patterns. The subject in this case must determine which of the tactile patterns in the series matches the visual target pattern 422 illustrated on the monitor 418.

In another tactile recognition test, the subject is presented a tactile test pattern using the tactile interface 402 and must identify on the monitor 418 which of a series of patterns was presented. In a more difficult tactile test, an incorrect tactile pattern 426 may be presented using the tactile interface 402 wherein the subject is required to identify which pins are not presented corresponding to a visually presented target pattern 422.

To adapt training difficulty, the spatial, temporal, and intensity parameters for the recognition test 420 may be altered. By way of example, the spatial parameters of the tactile input may be altered by varying the proximity and/or arrangement of the spatially orientated pins 404 and 406 for the target and foil tactile patterns. Alternatively, to introduce a higher level of difficulty, the similarity of the test tactile pattern to the target tactile pattern may be increased. To alter the temporal parameters, the duration presentation of the pattern to the user may be varied. Typically, as the duration is shortened, the test becomes more difficult. To vary the intensity of the testing, the height of the spatially oriented pins 404 and 406 may be manipulated. Alternatively, the maximum allowable force exerted on the spatially oriented pins 404 and 406 may be limited to limit the intensity of the tactile perception. Correspondingly, to adapt the testing to be more difficult, the maximum allowable force on a pin may then be decreased.

FIG. 4C illustrates a process 440 of training a human subject with the tactile testing apparatus 400 in accordance with one embodiment of the present invention. The process 440 typically begins with providing the subject with a target tactile pattern (442). For example, the tactile target pattern may be presented visually using the monitor 418. Subsequently, the subject is presented with a test tactile pattern (444) using the tactile interface 402 wherein the subject must indicate if the test tactile pattern matches the target tactile pattern (446).

Multiple test tactile patterns may be provided (loop 444/446/448). For example, various test tactile patterns may be repeatedly provided until the target tactile pattern is provided using the tactile interface 402 and the subject correctly identifies it. Alternatively, a test may include providing a predefined number of test tactile patterns, i.e., three tactile patterns, in which one or more of them corresponds to the target tactile pattern. The process 440 may also include feedback to the user indicative of their response to the test tactile pattern. Testing may then proceed (450), if desired, while adapting the test difficulty (452). For example, testing difficulty may be adapted by varying the response time to identify a test tactile pattern. For the process 440, the parameters need not be altered after every test. When the parameters are altered, a training or other suitable learning progression mechanism may be implemented to facilitate lasting changes in the somatosensory perception and motor control improvements. In one embodiment of the present invention, the tactile testing apparatus 400 is present in the user's home or other convenient location and a networked remote computer is used to administer the training. By remote testing in this manner, the practical inconveniences of prior art testing techniques are advantageously avoided.

Having briefly explained some exemplary exercises and testing methods suitable for the tactile testing apparatus 400, some preferable modifications and other alternatives will now be described.

The tactile testing apparatus 400 is also suitable for driving other somatosensory perception and motor control improvements. By way of example, a series of temporal varying patterns may be presented using the tactile interface 402 to drive temporal improvements in the differentiation of somatosensory information. An example of a temporally varying pattern is one in which the number of spatially orientated pins presented by the tactile interface 402 varies over time. Thus, a suitable test would require the individual to identify the number of pins as they are presented. Correspondingly, the test improves the ability to distinguish the temporal and spatial aspects of tactile sensing.

Figure 5A:
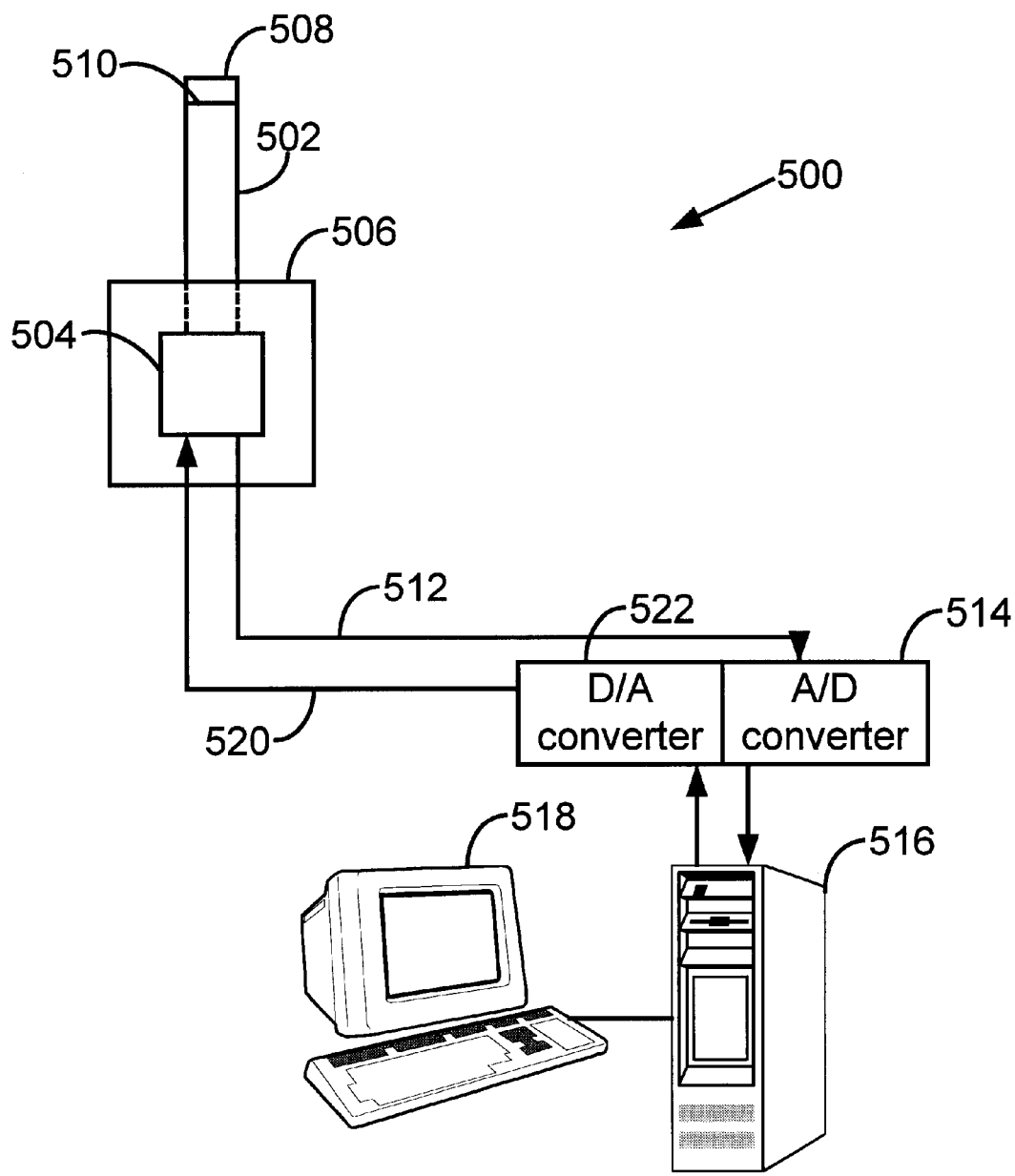
FIG. 5A illustrates a motor control tester suitable for driving somatosensory perception and motor control improvements in accordance with one embodiment of the present invention.

A third preferred embodiment of the present invention includes the use of an apparatus which requires an individual track the displacement of a probe. FIG. 5A illustrates a motor control tester 500 suitable for driving somatosensory perception and motor control improvements. The motor control tester 500 is particularly suitable for improving fine motor control of a finger and training to reduce the co-contraction of a motor pair.

The motor control tester 500 includes a probe 502 capable of linear motion. During testing, the subject is required to maintain contact with an upper surface 510 of the probe 502 as it moves. The exact motion and permissible contact may be specified by a particular test. Typically, as the permissible force is decreased, the testing becomes more difficult. The testing may also implement a tolerance to define acceptable force limits applied by the user. Again, as the tolerance decreases, the testing becomes more difficult. Alternatively, permissible contact with the probe 502 may be defined by a continuous minimum or force or displacement error.

A linear motor 504 is attached to the probe 502 and acts to actuate the probe 502 in its single degree of freedom. The linear motor 504 may be any suitable actuation providing position control, and force control if desired, for the probe 502 and is not necessarily limited to the linear motor 504. By way of example, a dc motor or pneumatic actuator may be used. The linear motor 504 is typically situated in a housing 506. The housing 506 acts to protect the linear motor 504 and other components of the motor control tester 500.

To permit feedback from the user, a force sensor 508 is disposed on an upper surface 510 of the probe 502. The force sensor 508 detects the force applied by the person's finger to the probe 502. It should be noted that the force sensor 508 is not limited to placement on the upper surface 510 of the probe 502. By way of example, the force sensor 508 may be coupled to the probe 502 within the housing 506. Alternatively, the current supplied to the linear motor 504 may be used as mechanism for detecting force applied by the user. Further, a position sensor may also be used to monitor the displacement of the probe 502. By way of example, the position sensor may be a linear encoder attached to the probe 502. Correspondingly, as one skilled in the art would appreciate, a hybrid force/position control may then be implemented to control motion of the probe 502 and obtain a response from the user.

In one embodiment, the force sensor 508 is simplified by using a binary contact sensor which simply detects the presence of contact with the upper surface 510 of the probe 502. To provide a tolerance of allowable error for the binary sensor, a spring may be added which permits a consistent force/distance tolerance error for the individual. In other words, when the spring is compressed, contact is established and the contact sensor signals a following error by the user. Further, a pair of springs may be used on either side of the correct response position of the probe 502 to allow a tolerance range for correct tracking by the person in either direction. Thus, a pair of contact sensors may be situated on either end of a tolerance range to provide binary detection of the person's ability to track the probe 502. In other words, once the springs are displayed a particular distance, i.e. a particular force based on the stiffness of the springs, a binary sensor or limit switch may then signal the tolerance has been exceeded.

A transmission line 512 relays information from the force sensor 508 to an A/D converter 514, which is in further communication with a computer 516. A transmission line 520 relays information from the computer 516 to a D/A converter 522, which is in further communication with the linear motor 504. The computer 516 is responsible for control of the linear motor 504 and the probe 502. Typically, a software program running on the computer 516 issues motion control parameters particular to an exercise. The software program and computer 516 may also be used to present training information to facilitate user interface using one or more peripheral devices. In a preferred embodiment, a monitor 518 displays visual feedback of the person's performance in the exercise.

The motor control tester 500 may implement a wide variety of motion parameters including displacement range of the probe 502, probe speed and a frequency range used in the testing. It should be noted that the frequency of the probe 502 is preferably not periodic and maintains substantial variability to require a continual level of engagement by the subject. By way of example, the motor control tester 500 may have a displacement range of 1 to 6 cm, probe speeds ranging from 1 cm/sec to 180 cm/sec, and a frequency range from 0.01 Hz to 10 Hz. In a preferred embodiment, the motor control tester 500 includes a displacement range of 2 to 4 cm, variable speeds ranging from 1 cm/sec to 150 cm/sec and a frequency range from 0.1 Hz to 10 Hz. Typically, as testing progresses, these parameters are adapted to the current motor control abilities of the human subject.

In one embodiment, as the probe 502 is moved, the person is required to follow and maintain a light contact with the upper surface 510 using a finger. As co-contraction in a motor pair is typically marked by deficiencies in force and position control of the flexors and extensors for a finger, training with the motor control tester 500 may be directed to testing and training the individual to relax both the flexors and extensors to alleviate co-contraction. In other words, the testing would require the person to apply a light force and follow the motor control tester 500 with temporal fidelity and suitable force intensity, which is at the limit of control permitted in the presence of the co-contraction. As training progresses and motor and/or sensory control improves, the testing may become more difficult, to drive continuous improvement.

Typically, training with the motor control tester 500 would include a battery of tests. A single test may require the subject to maintain contact until contact is lost. Upon inability to maintain contact, the individual would be required to re-establish suitable contact and proceed to maintain contact with potentially altered parameters. Alternatively, if the person is able to maintain contact for an extended duration, the testing parameters may be altered without breaking contact with the probe 502. Testing may proceed continuously for a sufficient amount of time and parameters may suitably adapt to achieve a desired training direction. By way of example, a training session may require an individual to test for two to ten minutes to improve temporal fidelity of the motor control of a finger. Alternatively, if the testing is administered to relax the individual for further training with another apparatus, five minutes of training with the motor control tester 500 may be sufficient.

The adaptation of parameters may be in any such manner to elicit the desired direction of improvement. If the individual maintains contact with the probe 502, the parameters may be adapted periodically while the individual maintains contact. For example, the parameters may be adapted every five to ten seconds or after a predetermined number of cycles based on the exercise. Preferably, continuous evaluation of the subject's performance may be implemented using the computer 514 to induce changes in the parameters at a rate in which the individual does not notice.

Figure 5B:
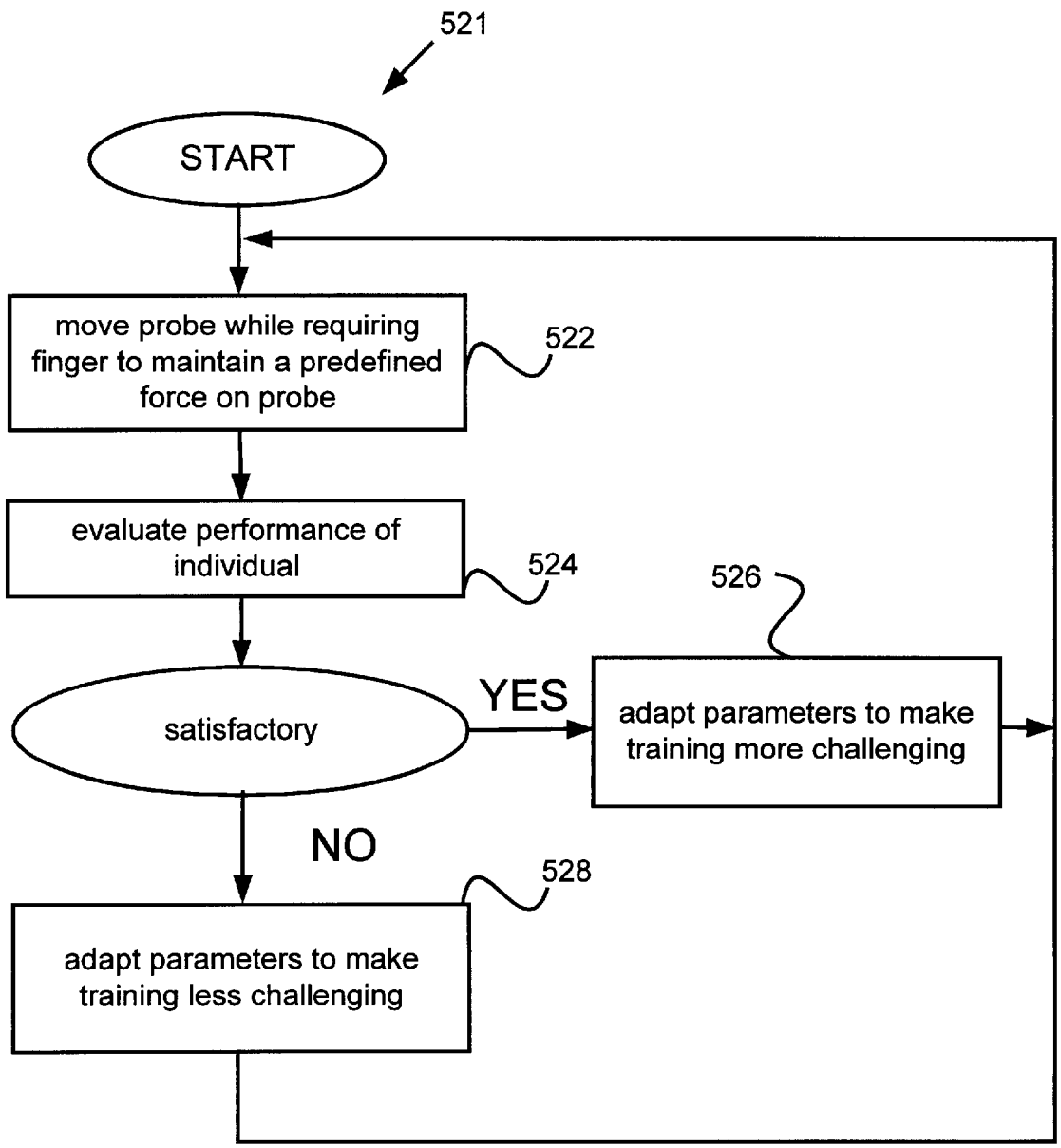
FIG. 5B illustrates an exemplary training process suitable for the motor control tester of FIG. 5A.

FIG. 5B illustrates an exemplary training process 521 suitable for the motor control tester 500. The training process 521 begins with a test at a predetermined level of difficulty (522). Preferably, the initial parameters correspond to a relatively easy set of parameters for the person, i.e., the person may apply a large force at a low frequency of the probe 502. Alternatively, the initial parameters may correspond to the performance of the individual from a previous training session.

The subject's performance on the motor control tester 500 is then evaluated. The evaluation may be whether the person has maintained allowable contact with the probe 502 or may include comparison against a benchmark (524). The benchmark may be, for example, the performance expected of an individual at a particular level of degraded motor control ability. Obviously, the exact benchmark depends on the nature of the exercises administered and may vary for an exercise as the person's ability improves. By way of example, requirements of the benchmark may include a predefined force to be continually maintained on the upper surface 510 over a certain number of tests.

If the subject's performance is below the benchmark or the person is unable to maintain suitable contact, the testing parameters are adapted to make the testing less difficult (528). By way of example, the required force of permissable contact may be increased. Alternatively, the frequency of the probe 502 may be reduced to make the testing less difficult. Subsequently, the subject may resume testing (522). Alternatively, if the performance is above the predefined benchmark, or the person is able to maintain suitable contact with the probe 502 for a particular number of cycles, the parameters of the testing may be adapted to make the testing more challenging (526). In this manner, improvements in the motor control abilities of the person may be made in an incremental and on-going basis. As input from the sensor 508 may include quantitative information with respect to the individual's performance, the adaptations to the testing parameters may be made based on quantitative feedback with respect to the individual's performance. In one embodiment of the present invention, the motor control tester 500 is present in the user's home or other convenient location and a networked remote computer is used to administer the training.

In a preferred embodiment, the motor control tester 500 is used to relax an opposing muscle pair in the beginning of a training session. By way of example, five to fifteen minutes may be adequate to relax a particular opposing muscle pair for further training. More specifically, ten minutes may be adequate to relax a particular opposing muscle pair.

Although the training with motor control tester 500 has been referred to with respect to one finger, the training is also applicable to other testing variations related to improving motor control deficits. By way of example, two fingers may be required to maintain contact with one or more independent probes 502 during testing. Further, as testing progresses, the number of fingers may change to reflect motor control changes for the individual. In a preferred embodiment, a constraint or resting surface may be used to rest a portion of the arm in order to restrict motion to a particular opposing muscle pair. In other words, the constraint or resting device is used to isolate an opposing muscle pair, thereby restricting testing to the motion of a finger as opposed to motion including a finger and wrist.

Having briefly illustrated three preferred apparatus and numerous exemplary exercises and training methods, some of the above mentioned features will now be expanded upon to illustrate some of the training aspects of the present invention.

The training to improve motor control deficits in accordance with the present invention may use more than one apparatus. In a preferred training method, all three of the aforementioned testing apparatus are implemented. For example, training with the motor control tester 500 may be implemented in a training session in order to relax the individual for further training with the other two apparatus.

In one embodiment of the present invention, testing is preferably administered for 1 to 1.5 hour per day, 5 days per week, for 6 to 8 weeks. It is obvious that these rates may be varied considerably based on the needs of the individual. In one application of testing, hundreds of individual exercises may be administered in a single training session, although this number may change based on the duration of individual exercises and the duration of testing for the day. Nevertheless, the number of exercises administered should be sufficiently high to drive changes for the motoric and/or sensory deficiencies. In addition, the testing with each of the apparatus may proceed a sufficient number of repetitions to drive the desired improvements in the deficit being trained on the apparatus, i.e. to reach a desired training goal.

For all three testing apparatus, various modifications may be made to facilitate a particular training direction. By way of example, the contact surfaces for each of the devices may be altered. More specifically, a rough tip may be applied to the probe 502 to increase the tactile feedback for the motor control tester 500. Alternatively, to alter the intensity of the tactile input for the spatially oriented pins 404 and 406 of the tactile testing apparatus 400, the surface of the pins may be varied.

The apparatus of the present invention may also be used to assess motor control deficits. In this manner, a battery of interactive motor skill tests is administered in which the performance response attained from the tests is used to build an assessment of the motor control deficits for an individual. Typically, the tests may comprise a set of computer-implemented tasks and exercises which provide an indication of the individual's sensory and motor deficits. By way of example, the tests may be administered before training to get a pre-training indication of the individual's deficits as well as after periodic training for progressive comparison.

An advantage of the present invention is that the quantitative basis of the computer-implemented methods allow improved diagnosis, assessment and treatment the motor control deficits. As the computer-implemented tests may engage the subject and obtain assessment at a resolution greater than personal awareness or conventional qualitative methods by a health care professional, this may advantageously enable a more accurate meter of motor control deficit progression and a better monitoring tool for treatment efficacy.

As mentioned earlier, the interactive behavioral exercises may be chosen such that they induce a high level of engagement from the user. Correspondingly, computer-implemented animations and entertainment methods may be implemented to present the exercise information using any of the apparatus. In one embodiment, the testing is disguised in a computer game. Alternatively, animations may be used, for example, in the reward of correct responses.

At the same time, the exercises may be chosen and adapted such that the individual is rewarded for correct performances a substantial percent of the time (e.g., about 80% or more in one embodiment). Accordingly, the exercises may be adjusted automatically by the computer, responsive to the individual's performance in a training session in order to keep the tests interesting and suitably challenging. Between training sessions, the testing parameters may be altered to accommodate the motor deficits determined from the most recent training session. It should be borne in mind that the above tests are illustrative and not meant to be restrictive with respect to what exercise information is presented, which parameters are used and how they may be altered.

The proposed invention also covers computer readable medium that includes instructions for treatment as described above. Yet another example of the present invention is a system for delivering computer readable instructions such as transmission, over a signal transmission medium, of signals representative of instructions for remote high frequency motor skills and somatosensory perception training. In this manner, the present invention may be implemented using a home computer or in any other convenient manner.

Advantageously, the computer-implemented methods allow treatment to be remotely performed at home, removing the requirement of time consuming, inconvenient and potentially prohibitive travel to a testing center; thus facilitating more frequent treatment and assessment. Alternatively, the present invention may allow a health care professional to obtain, evaluate and periodically monitor training data from one or more individuals who are training away from the testing center.

The proposed methods are not obvious in view of the prior art since the prior art does not suggest improving somatosensory feedback as a means of treating motor control deficits. In addition, the prior art does not flexibly adapt treatment to improvements in the temporal, spatial and intensity resolution of somatosensory feedback.

While this invention has been described in terms of several preferred embodiments, there are alterations, permutations, and equivalents which fall within the scope of this invention. By way of example, although only A/D and D/A converters have been shown in the testing apparatus, amplifiers and other design hardware may be included as one skilled in the art would appreciate. Alternatively, the number and arrangement of pins for the tactile interface 402 may be varied and is not limited to the number and arrangement described with respect to FIGS. 4A–B. In addition, although testing has been described with respect to training one or more fingers, the apparatus of the present invention are also applicable to thumbs or other surface capable of receiving tactile information. Further, the proposed apparatus are not limited strictly to the treatment of the particular motor control deficits and diseases listed herein. By example, motor control deficits related to Parkinson's disease may be treated with the apparatus listed above. It is therefore intended that the following appended claims be interpreted as including all such alterations, permutations, and equivalents as fall within the true spirit and scope of the present invention.

What is claimed is:

1. A computer-implemented method for improving one of a somatosensory perception and a motor control deficit for a human subject using a computer-implemented training apparatus, said computer-implemented method comprising:
   (a) administering, using said computer-implemented training apparatus, a training regime including one of a set of somatosensory and motor control exercises to said human subject, said training regime having sufficient intensity to affect a lasting improvement in said one of a somatosensory perception and motor control deficit within said human subject;
   (b) obtaining, using said computer-implemented training apparatus, a performance response of said human subject responsive to said one of a set of somatosensory and motor control exercises;
   (c) altering, using said computer-implemented training apparatus, one or more parameters pertaining to said one of a set of somatosensory and motor control exercises, wherein said altering of said one or more parameters is performed responsive to said performance response and is configured to facilitate improving said one of a somatosensory perception and a motor control deficit within said human subject; and
   (d) repeating at least (a) for a sufficient number of repetitions to affect said lasting improvement in said one of a somatosensory perception and a motor control deficit.

2. The computer-implemented method of claim 1 wherein said altering said one or more parameters is performed responsive to quantitative information ascertained from said performance response.

3. The computer-implemented method of claim 1 wherein said altering said one or more parameters includes altering the spatial, temporal or intensity parameters of said one of a set of somatosensory and motor control exercises.

4. The computer-implemented method of claim 1 wherein said one of a somatosensory perception and a motor control deficit is a motor control deficit.

5. The computer-implemented method of claim 1 wherein said one of a somatosensory perception and a motor control deficit is caused by stroke.

6. The computer-implemented method of claim 1 wherein said performance response is based on at least one of tactile perception, kinesthetic perception and proprioception.

7. The computer-implemented method of claim 1 wherein said altering said one or more parameters includes one of using the same one of a set of somatosensory and motor control exercises in said training regime with more difficult parameters and using at least one different somatosensory and motor control exercise in said one of a set of somatosensory and motor control exercises.

8. The computer-implemented method of claim 1 wherein said one of a set of somatosensory and motor control exercises includes an exercise involving one or more of the human subject's fingers.

9. The computer-implemented method of claim 1 wherein said one of a somatosensory perception and a motor control deficit is a somatosensory perception deficit.

10. The computer-implemented method of claim 1 wherein said administering said training regime includes administering at least 100 somatosensory and motor control exercises in a day.

11. The computer-implemented method of claim 1 wherein said one of a set of somatosensory and motor control exercises is directed to elicit a high level of engagement from said human subject.

12. The computer-implemented method of claim 11 wherein said one of a set of somatosensory and motor control exercises includes computer-implemented graphics.

13. The computer-implemented method of claim 1 wherein said altering of said one of a set of somatosensory and motor control exercises is directed to present a continual challenge.

14. The computer-implemented method of claim 1 wherein said computer-implemented training apparatus includes a somatosensory and motor control training device for improving one of a somatosensory perception deficit and a motor control deficit for a human subject, said device comprising:
   a plurality of force sensors situated in proximity such that each may receive one or more fingers from a hand of said human subject, said plurality of force sensors capable of force feedback from said one or more fingers; and
   a processor in electrical communication with said plurality of force sensors.

15. The computer-implemented method of claim 14 wherein said plurality of force sensors have a variable compliance.

16. The computer-implemented method of claim 14 wherein said processor is included in a computer.

17. The computer-implemented method of claim 16 wherein said computer is used for assessment of said one of a somatosensory perception deficit and motor control deficit.

18. The computer-implemented method of claim 14 further including a strain relief material or a textured material attached to said plurality of force sensors.

19. The computer-implemented method of claim 1 wherein said computer-implemented training apparatus includes a somatosensory and motor control training device for improving one of a somatosensory perception deficit and a motor control deficit for a human subject, said device comprising:
   a set of pins, wherein each pin is capable of independent linear displacement;
   a set of actuators coupled to said set of pins; and
   a processor in electrical communication with said set of actuators.

20. The computer-implemented method of claim 19 further including a latching mechanism coupled to said set of actuators.

21. The computer-implemented method of claim 19 wherein said set of pins is arranged in a substantially rectangular array.

22. The computer-implemented method of claim 19 wherein said processor is included in a computer.

23. The computer-implemented method of claim 22 wherein said computer is used for assessment of said one of a somatosensory perception deficit and motor control deficit.

24. The computer-implemented method of claim 22 wherein said one of a set of somatosensory and motor control exercises is used to train tactile perception by said human subject.

25. The computer-implemented method of claim 1 wherein said computer-implemented training apparatus includes a somatosensory perception and motor control training device for improving one of a somatosensory perception deficit and a motor control deficit for a human subject, said device comprising:
   a probe capable of linear displacement;
   an actuator coupled said probe;
   a sensor coupled to said probe; and a processor in electrical communication with said actuator and said sensor.

26. The computer-implemented method of claim 25 wherein the sensor is a force sensor.

27. The computer-implemented method of claim 26 wherein the force sensor is a binary force sensor.

28. The computer-implemented method of claim 27 further including a spring coupled to said probe.

29. The computer-implemented method of claim 25 wherein the sensor is a position sensor coupled to said probe.

30. The computer-implemented method of claim 25 wherein said processor is included in a computer.

31. The computer-implemented method of claim 30 wherein said device includes a second probe.

32. The computer-implemented method of claim 25 wherein said probe has a displacement range from 1 to 6 centimeters, a speed from 1 to 8 centimeters/second and a frequency of 0.01 to 10 Hertz.

33. The computer-implemented method of claim 25 wherein the motion of said probe follows a non-periodic waveform for an exercise implemented with said device.

34. A computer readable medium including instructions for improving one of a somatosensory perception and a motor control deficit for a human subject using a computer-implemented training apparatus, said instructions comprising:
 (a) instructions for administering, using said computer-implemented training apparatus, a training regime including one of a set of somatosensory and motor control exercises to said human subject, said training regime having sufficient intensity to affect a lasting improvement in said one of a somatosensory perception and motor control deficit within said human subject;
 (b) instructions for obtaining, using said computer-implemented training apparatus, a performance response of said human subject responsive to said one of a set of somatosensory and motor control exercises;
 (c) instructions for altering, using said computer-implemented training apparatus, one or more parameters pertaining to said one of a set of somatosensory and motor control exercises, wherein said altering of said one or more parameters is performed responsive to said performance response and is configured to facilitate improving said one of a somatosensory perception and a motor control deficit within said human subject; and
 (d) instructions for repeating at least (a) for a sufficient number of repetitions to affect said lasting improvement in said one of a somatosensory perception and a motor control deficit.

35. A computer implemented method for delivering computer readable instructions configured to improve one of a somatosensory perception and a motor control deficit for a human subject using a computer-implemented training apparatus, said instructions comprising:
 (a) transmitting, over a signal transmission medium, signals representative of instructions for administering, using said computer-implemented training apparatus, a training regime including one of a set of somatosensory and motor control exercises to said human subject, said training regime having sufficient intensity to affect a lasting improvement in said one of a somatosensory perception and motor control deficit within said human subject;
 (b) transmitting, over a signal transmission medium, signals representative of instructions for obtaining, using said computer-implemented training apparatus, a performance response of said human subject responsive to said one of a set of somatosensory and motor control exercises;
 (c) transmitting, over a signal transmission medium, signals representative of instructions for altering, using said computer-implemented training apparatus, one or more parameters pertaining to said one of a set of somatosensory and motor control exercises, wherein said altering of said one or more parameters is performed responsive to said performance response and is configured to facilitate improving said one of a somatosensory perception and a motor control deficit within said human subject; and
 (d) transmitting, over a signal transmission medium, signals representative of instructions for repeating at least (a) for a sufficient number of repetitions to affect said lasting improvement in said one of a somatosensory perception and a motor control deficit.

36. A computer-implemented method for improving one of a somatosensory perception and a motor control deficit for a human subject, said computer-implemented method comprising:
 (a) receiving instructions from a first computer to execute a first set of code at a second computer, said first computer being coupled to said second computer via a computer network, said first set of code being configured to administer a training regime including one of a set of somatosensory and motor control exercises to said human subject, said training regime having sufficient intensity to affect a lasting improvement in said one of a somatosensory perception and motor control deficit within said human subject;
 (b) transmitting computer commands from the second computer to the first computer to carry out the one of a set of somatosensory and motor control exercises at a user interface coupled to the first computer;
 (c) obtaining, using the first computer, a performance response of said human subject responsive to said one of a set of somatosensory and motor control exercises;
 (d) altering, using one of the first computer and the second computer, one or more parameters pertaining to said one of a set of somatosensory and motor control exercises, wherein said altering of said one or more parameters is performed responsive to said performance response and is configured to facilitate improving said one of a somatosensory perception and a motor control deficit within said human subject; and
 (e) transmitting computer commands for repeating at least (a) for a sufficient number of repetitions to affect said lasting improvement in said one of a somatosensory perception and a motor control deficit.

37. The method of claim 36 further including providing said performance response to a health care professional using one of the first computer and the second computer.

* * * * *